(12) United States Patent
Saracen et al.

(10) Patent No.: US 8,160,205 B2
(45) Date of Patent: Apr. 17, 2012

(54) ROBOTIC ARM FOR PATIENT POSITIONING ASSEMBLY

(75) Inventors: Michael J. Saracen, Oakland, CA (US); Aaron W. Carrano, San Jose, CA (US); Toby D. Henderson, Rockford, IL (US)

(73) Assignee: Accuray Incorporated, Sunnyvale, CA (US)

( * ) Notice: Subject to any disclaimer, the term of this patent is extended or adjusted under 35 U.S.C. 154(b) by 1513 days.

(21) Appl. No.: 11/129,122

(22) Filed: May 13, 2005

(65) Prior Publication Data

US 2005/0234327 A1 Oct. 20, 2005

Related U.S. Application Data

(63) Continuation-in-part of application No. 10/881,315, filed on Jun. 30, 2004, now Pat. No. 7,860,550.

(60) Provisional application No. 60/560,318, filed on Apr. 6, 2004.

(51) Int. Cl.
*G21K 5/10* (2006.01)
(52) U.S. Cl. ............... 378/69; 378/35; 378/68; 600/427
(58) Field of Classification Search .................... 378/65, 378/68, 69; 600/427
See application file for complete search history.

(56) References Cited

U.S. PATENT DOCUMENTS

| | | | |
|---|---|---|---|
| 2,295,006 A | 9/1942 | Philips | |
| 2,787,506 A | 4/1957 | Travisano | |
| 3,069,543 A | 12/1962 | Sazavsky | |
| 3,082,322 A | 3/1963 | Koerner | |
| 3,262,133 A | 7/1966 | Beitzel | |
| 3,640,520 A | 2/1972 | Wieland et al. | |
| 3,806,109 A | 4/1974 | Weber et al. | |
| 3,997,926 A | 12/1976 | England | |
| 4,259,756 A | 4/1981 | Pace | |
| 4,579,323 A | 4/1986 | Brendl et al. | |
| 4,603,845 A | 8/1986 | Schmedemann | |
| 4,618,133 A | 10/1986 | Siczek | |
| 4,672,697 A | 6/1987 | Schurch | |
| 4,697,802 A | 10/1987 | Brendl et al. | |
| 4,749,177 A | 6/1988 | Schafer et al. | |
| 4,841,585 A | 6/1989 | Masuzawa | |
| 4,872,657 A | 10/1989 | Lussi | |
| 5,022,810 A | 6/1991 | Sherrow et al. | |
| 5,044,354 A * | 9/1991 | Goldhorn et al. | 601/4 |

(Continued)

FOREIGN PATENT DOCUMENTS

EP 1121957 8/2001

(Continued)

OTHER PUBLICATIONS

Linear Accelerators (5 pages), Sep./Oct. 2003, from Imaging Technology News, Sep./Oct. 2003, vol. 43, No. 5, www.ITNonline.net, + Cover page, Table of Contents (2 pages), 7 pages total.

(Continued)

*Primary Examiner* — Long V. Le
*Assistant Examiner* — Ellsworth Weatherby
(74) *Attorney, Agent, or Firm* — Lowenstein Sandler PC

(57) ABSTRACT

A robotic patient positioning assembly including a patient treatment couch, and a robotic arm coupled to the patient treatment couch. The robotic arm is configured to move the patient treatment couch along five rotational degrees of freedom and one substantially vertical, linear degree of freedom.

23 Claims, 16 Drawing Sheets

U.S. PATENT DOCUMENTS

| | | | |
|---|---|---|---|
| 5,207,223 | A | 5/1993 | Adler |
| 5,299,334 | A | 4/1994 | Gonzalez |
| 5,345,632 | A | 9/1994 | Langenaeken et al. |
| 5,361,436 | A | 11/1994 | Hahn |
| 5,386,453 | A | 1/1995 | Harrawood et al. |
| 5,427,097 | A | 6/1995 | Depp |
| 5,499,415 | A | 3/1996 | McKenna |
| 5,572,569 | A | 11/1996 | Benoit et al. |
| 5,613,254 | A | 3/1997 | Clayman et al. |
| 5,619,763 | A | 4/1997 | Randolph et al. |
| 5,655,238 | A | 8/1997 | Stickley et al. |
| 5,744,728 | A | 4/1998 | Suita et al. |
| 5,790,996 | A | 8/1998 | Narfstrom |
| 5,820,553 | A | 10/1998 | Hughes |
| 5,825,843 | A | 10/1998 | Kobayashi |
| 5,983,424 | A | 11/1999 | Naslund |
| 6,094,760 | A | 8/2000 | Nonaka et al. |
| 6,125,164 | A | 9/2000 | Murphy et al. |
| 6,138,302 | A | 10/2000 | Sashin et al. |
| 6,217,214 | B1 | 4/2001 | Cabral et al. |
| 6,222,544 | B1 | 4/2001 | Tarr et al. |
| 6,279,579 | B1 | 8/2001 | Riaziat et al. |
| 6,385,286 | B1 | 5/2002 | Fitchard et al. |
| 6,416,219 | B1 | 7/2002 | Pflaum et al. |
| 6,484,332 | B2 | 11/2002 | Korver, II et al. |
| 6,501,981 | B1 | 12/2002 | Schweikard et al. |
| 6,502,261 | B1 | 1/2003 | Harwood |
| 6,516,046 | B1 | 2/2003 | Frohlich et al. |
| 6,524,246 | B1 | 2/2003 | Kelly et al. |
| 6,617,852 | B1 | 9/2003 | Danby et al. |
| 6,651,279 | B1 | 11/2003 | Muthuvelan |
| 6,810,108 | B2 | 10/2004 | Clark et al. |
| 6,826,254 | B2 | 11/2004 | Mihara et al. |
| 6,865,253 | B2 | 3/2005 | Blumhofer et al. |
| 6,889,695 | B2 * | 5/2005 | Pankratov et al. ............ 128/898 |
| 7,046,765 | B2 | 5/2006 | Wong et al. |
| 7,154,991 | B2 | 12/2006 | Earnst et al. |
| 7,166,852 | B2 | 1/2007 | Saracen et al. |
| 7,173,265 | B2 | 2/2007 | Miller et al. |
| 7,298,385 | B2 * | 11/2007 | Kazi et al. ..................... 345/633 |
| 2002/0072813 | A1 | 6/2002 | Ito |
| 2002/0077545 | A1 | 6/2002 | Takahashi et al. |
| 2002/0188194 | A1 | 12/2002 | Cosman |
| 2002/0193685 | A1 | 12/2002 | Mate |
| 2003/0048875 | A1 | 3/2003 | Mihara et al. |
| 2004/0172756 | A1 | 9/2004 | Somasundaram |
| 2005/0027285 | A1 | 2/2005 | Ritter et al. |
| 2005/0085710 | A1 | 4/2005 | Earnst et al. |
| 2005/0226377 | A1 | 10/2005 | Wong et al. |
| 2005/0228255 | A1 | 10/2005 | Saracen et al. |
| 2005/0234327 | A1 | 10/2005 | Saracen et al. |
| 2006/0002511 | A1 * | 1/2006 | Miller et al. .................... 378/65 |
| 2006/0245543 | A1 * | 11/2006 | Earnst et al. .................... 378/65 |

FOREIGN PATENT DOCUMENTS

| | | |
|---|---|---|
| JP | 1-214373 | 8/1989 |
| JP | 4-348895 A | 12/1992 |
| JP | 5111542 | 5/1993 |
| JP | 6-182653 A | 7/1994 |
| JP | 2001-238923 | 9/2001 |
| JP | 2002253687 A | 9/2002 |
| JP | 2003-135539 | 5/2003 |
| JP | 2003-210594 | 7/2003 |
| JP | 2004166975 A | 6/2004 |
| WO | WO 9413205 | 6/1994 |
| WO | WO 9927839 | 6/1999 |
| WO | WO 2005/018734 | 3/2005 |

OTHER PUBLICATIONS

International PCT Search Report and Written Opinion, PCT/US06/18017, International filing date May 9, 2006, mailing date Jan. 11, 2007, (13 pages).

Alejandro Mazal et al., "Robots in patient positioning for external radiotherapy", presentation, 46th American Association of Physicists in Medicine Annual Meeting, Pittsburgh, Jul. 2004.

"Adept Technology Announces Extension of SmartServo Architecture to SCARA Robots", Adept Technology, Inc., News Article, Sep. 18, 2002, 2 pages.

"Adept Technology Introduces Four New SCARA Robots with Adept's SmartServo Architecture", Adept Technology, Inc.—News Article, Apr. 14, 2003, 2 pages.

"EC Series SCARA Robots", Seiko EC SCARA Robots, 2003, Epson America, Inc., 3 pages, downloaded Nov. 18, 2004, http://www.seikorobots.com/products/ecrbts.htm.

"EH Series SCARA Robots", Epson EH SCARA Robots, 2 pages, downloaded Nov. 18, 2004, http://www.robots.epson.com/products/ehrbts.htm.

"SCARA Robot—Adept Cobra s600", SCARA Robot—Adept Cobra s600—tabletop factory automation, 2 pages, downloaded Nov. 18, 2004, http://www.adept.com/main/products/robots/cobra_s600.shtml 2 pages.

Adept Cobra s600 Robot with CS or CX (90565-00x), Adept Technology, Inc., Nov. 5, 2004, 5 pages.

"Adept SmartCartesian™", Adept Technology, Inc., Mar. 26, 2002, 1 page.

"HS & HM Series SCARA Robots", Motoman, Solutions in Motion, 4 pages, 2002 Motoman, Inc. Sep. 2002.

"EPH4000" Motoman, Solutions in Motion, 2 pages, 2004 Motoman, Inc., Feb. 2004.

"AdeptXL SCARA Robots", downloaded Nov. 30, 2004, http://www.adept.com/main/products/robots/AdeptXL.shtml, 1 page.

"AdeptThree XL SCARA Robot", 2000-2004, Adept Technology, Inc., downloaded Nov. 30, 2004, http://www.adept.com/main/products/robots/AdeptThree.shtml, 1 page.

Pro Six (6-Axis), Epson Pro Six 6-Axis Robots (also called Vertical Articulated robots), 3 pages, downloaded Nov. 30, 2004, http://www.robots.epson.com/products/prosixrbts.htm.

"E2H SCARA Robots", Epson E2H SCARA Robots, downloaded Nov. 30, 2004, http://www.robots.epson.com/products/e2hrbts.htm, 3 pages.

"UP6" Payload: 6 kg, Motoman, Solutions in Motion, 2 pages., 2003 Motoman Inc., Oct. 2003.

"UP2OMN" Payload: 20 kg, Motoman, Solutions in Motion, 2 pages, 2004 Motoman Inc., Mar. 2004.

"HP20" Payload: 20 kg, Motoman, Solutions in Motion, 2 pages, 2004 Motoman Inc., Apr. 2004.

"Motoman-CR50", Type: YR-CR50-A00, 1 page, http://www.motoman.com/products/robots/default.htm, 2001-2005, Motoman Inc., downloaded May 12, 2005.

"Welding One Step Ahead, Linear Units", Kuka Robot Group, downloaded Apr. 20, 2005, http://www.kuka.com/en/products/addons/linearunits/start.htm, 1 page.

"KR6", Kuka Robot Group, downloaded Nov. 17, 2004, http://www.kuka.com/en/products/robots/low/kr6/start.htm, 1 page.

"KR16", Kuka Robot Group, downloaded Nov. 17, 2004, http://www.kuka.com/en/products/robots/low/kr16/start.htm, 1 page.

"KR 16 KS" Kuka Robot Group, downloaded Nov. 17, 2004, http://www.kuka.com/en/products/robots/low/kr16_ks/start.htm, 1 page.

"KR 16 L6", Kuka Robot Group, downloaded Nov. 17, 2004, http://www.kuka.com/en/products/robots/low/kr16_16/start.htm, 1 page.

"KR 30-3", Kuka Robot Group, downloaded Nov. 17, 2004, http://www.kuka.com/en/products/robots/medium/kr30_3/start.htm 1 page.

KR 30-3 KS, Kuka Robot Group, downloaded Nov. 17, 2004, http://www.kuka.com/en/products/robots/medium/kr30_3 ks/start.htm, 1 page.

KR 30 HA (High Accuracy), Kuka Robot Group, downloaded Nov. 17, 2004, http://www.kuka.com/en/products/robots/medium/kr30_ha/start.htm, 1 page.

"KR 60-3", Kuka Robot Group, downloaded Nov. 17, 2004, http://www.kuka.com/en/products/robots/medium/kr60_3/start.htm, 1 page.

"KR 60-3 KS", Kuka Robot Group, downloaded Nov. 17, 2004, http://www.kuka.com/en/products/robots/medium/kr60_3_ks/start.htm, 1 page.

KR 100 P (Series 2000), Kuka Robot Group, downloaded Nov. 17, 2004, http://www.kuka.com/en/products/robots/hiqh/kr100_p_2000/start.htm, 1 page.

KR 150 K (Series 2000), Kuka Robot Group, downloaded Nov. 17, 2004, http://www.kuka.com/en/products/robots/hiqh/kr150_k_2000/start.htm, 1 page.

"KR 500 570 PA/1", Kuka Robot Group, downloaded Nov. 17, 2004, http://www.kuka.com/en/products/robots/heavy/kr500_570_pa/start.htm, 1 page.

"Linear Units", Kuka Robot Group, downloaded Nov. 30, 2004, http://www.kuka.com/cgi-bin/MsmGo.exe?grab_id=11&page_id=9375232&query=Linear+Units&hiword=LINEAREN+LINEARLY+ Linear+UNIT+UNITE+UNITED+Units+, 1 page.

"KR 500 570 PA/1", Kuka Robot Group, downloaded Nov. 30, 2004, http://www.kuka.com/en/products/robots/heavy/kr500_570_pa/start.htm, 1 page.

"iThemba LABS Medical Radiation Group, New Treatment Station, Non-Orthogonal Beam Lines for Proton Therapy", Seite 1 von 2, downloaded Aug. 3, 2004, http://www.medrad.nac.ac.za/npther.htm, 12 pages.

KR 210-2 (Series 2000), Kuka Robots USA, downloaded Jan. 21, 2005, http://www.kuka.com/usa/en/products/robots/hiqh/kr210_2_2000/start.htm, 1 page.

KR360/1, KR360 450 PA/1, KR 360 L150 P/1, KR 500/1, KR 500 570 PA/1, Mar. 1, 2005, cover sheet and pp. 13-22, 33-58, Mar. 1, 2005.

"CyberKnife", Stereotactic Radiosurgery System using image-guided robotics, downloaded Nov. 16, 2004, http://www.accuray.com/ck/deliv18.htm, 3 pages.

E.A. de Kock et al., "Integrating an industrial robot and multi-camera computer vision systems into a patient positioning system for high-precision radiotherapy", Wednesday, Mar. 24, 2004, 6 pages, ISR 2004 Symposium, Mar. 23-26, 2004.

Linac Scalpel, "RadioCameras™ System, Frameless Stereotactic Radiotherapy and Radiosurgery," Zmed Inc., 2001.

TomoTherapy Incorporated, "The Tomo® Advantage: TomoImage™", 2003.

TomoTherapy Incorporated, "A True Integrated Treatment System", 2003.

BrainLAB Radiotherapy Solutions, "A good idea perfected, ExacTRAC$^{xray6D}$, BrainLAB's unique X-Ray based targeting technology. Available as an upgrade to your existing Linac", 2003 BrainLAB AG.

Neurosurgery News, New Products/Press Releases, "Elekta Receives FDA Clearance for Elekta Synergy™, New radiotherapy system from Elekta combines x-ray volume imaging and treatment in a single platform", Fall 2003, pp. 17-18.

North American Scientific, NOMOS Radiation Oncology Division, "IMRT/IMRS Delivery System", 2003.

Varian Medical Systems, Oncology Systems, Treatment Delivery, Exact Couch™ Couch and Indexed Immobilization™, 1999-2005 Varian Medical Systems, Inc.

Milton K. Woo, Bryan Kim, "An investigation of the reproducibility and usefulness of automatic couch motion in complex radiation therapy techniques", Journal of Applied Clinical Medical Physics, vol. 3, No. 1, Winter 2002, pp. 46-50.

PCT International Preliminary Report on Patentability (Chapter 1 of the Patent Cooperation Treaty), PCT/US2006/018017 filed May 9, 2006, mailed Apr. 24, 2008.

Susan B. Klein, "Status of the Proton Therapy Project at IUCF and the Midwest Proton Radiotherapy Institute", AIP Conference Proceedings, Aug. 26, 2003—vol. 680, pp. 1081-1085.

A.N. Schreuder and A. Muller, "Development of a patient positioning system for high precision radiotherapy", Dec. 28, 2004, 4 pages.

European Search Report, 04782483.4-2305, PCT/US2004028011 dated Oct. 16, 2007.

Fourth Office Action for Chinese Patent Application No. 200580018430.5, Date of Issue: Dec. 25, 2009, 28 pages.

Chinese Patent Application No. 200680025045.8, First Notification of Office Action issued Jun. 5, 2009, 5 pages.

U.S. Appl. No. 10/687,860, filed Oct. 17, 2003, Final Office Action mailed Jan. 24, 2006, 16 pages.

U.S. Appl. No. 10/687,860, filed Oct. 17, 2003, Notice of Allowance mailed Apr. 5, 2006, 5 pages.

U.S. Appl. No. 10/687,860, filed Oct. 17, 2003, Office Action mailed May 31, 2005, 13 pages.

U.S. Appl. No. 11/478,753, filed Jun. 29, 2006, Office Action mailed Dec. 18, 2006, 21 pages.

U.S. Appl. No. 11/478,753, filed Jun. 29, 2006, Advisory Action mailed Aug. 21, 2007, 4 pages.

U.S. Appl. No. 11/478,753, filed Jun. 29, 2009, Final Office Action mailed Jun. 12, 2007, 15 pages.

U.S. Appl. No. 11/478,753, filed Jun. 29, 2006, Final Office Action mailed Oct. 23, 2008, 14 pages.

U.S. Appl. No. 11/478,753, filed Jun. 29, 2006, Office Action mailed May 29, 2008, 18 pages.

U.S. Appl. No. 11/478,753, filed Jun. 29, 2006, Office Action mailed Nov. 30, 2007, 13 pages.

U.S. Appl. No. 10/881,315, filed Jun. 30, 2004, Advisory Action mailed Jul. 17, 2008, 3 pages.

U.S. Appl. No. 10/881,315, filed Jun. 30, 2004, Final Office Action mailed Jan. 16, 2009, 13 pages.

U.S. Appl. No. 10/881,315, filed Jun. 30, 2004, Final Office Action mailed Feb. 6, 2008, 18 pages.

U.S. Appl. No. 10/881,315, filed Jun. 30, 2004, Office Action mailed Feb. 23, 2007, 24 pages.

U.S. Appl. No. 10/881,315, filed Jun. 30, 2004, Office Action mailed Jun. 10, 2009, 18 pages.

U.S. Appl. No. 10/881,315, filed Jun. 30, 2004, Office Action mailed Aug. 29, 2008, 14 pages.

International Search Report, International Searching Authority, PCT/US2004/28011, Oct. 31, 2005, 3 pages.

Written Opinion of the International Searching Authority, International Searching Authority, PCT/US2004/28011, Oct. 31, 2005, 5 pages.

PCT International Preliminary Report on Patentability, PCT/US2004/28011, Mar. 15, 2006, 5 pages.

PCT International Preliminary Report on Patentability, PCT/US2006/18017, Apr. 15, 2008, 7 pages.

PCT International Search Report, PCT/US05/11469 filed Apr. 5, 2005, mailed Mar. 26, 2007.

PCT Written Opinion of the International Searching Authority, PCT/US05/11469 filed Apr. 5, 2005, mailed Mar. 26, 2007.

PCT International Preliminary Report on Patentability, PCT/US2005/011469 filed Apr. 5, 2005, mailed Apr. 26, 2007.

Final Office Action for U.S. Appl. No. 11/478,753, mailed Jun. 12, 2007, 17 pages.

Response to Rule 312 Communication for U.S. Appl. No. 10/881,315, mailed Jun. 2, 2010, 2 pages.

Notice of Allowance for U.S. Appl. No. 10/881,315, mailed Apr. 1, 2010, 23 pages.

Japanese Office Action mailed Aug. 30, 2011 for Japanese Patent Application No. 2008-511299, 3 pages.

* cited by examiner

ROBOTIC ARM FOR PATIENT POSITIONING ASSEMBLY

RELATED APPLICATION

This application is a continuation in part of application Ser. No. 10/881,315, filed Jun. 30, 2004, now U.S. Pat. No. 7,860,550 which claims the benefit of U.S. Provisional Application No. 60/560,318, filed Apr. 6, 2004, which are incorporated by reference herein.

TECHNICAL FIELD

Embodiments of the present invention pertain to the field of patient positioning assembly for medical operations.

BACKGROUND

Conventional robots are designed to do exactly the same thing over and over again, such as in an assembly line for assembly. These robots are programmed and configured to repeat a given motion to perform a specific function. Robots are often implemented to perform a lot of functions, more efficiently, and often more precisely than humans.

Conventional robots, typically, include one or two robotic arms. These robotic arms can have multiple segments that help facilitate movement in differing degrees of freedom (DOF). Some conventional robots employ a computer to control the segments of the robotic arm by activating rotation of individual step motors connected to corresponding segments. Other designs may use hydraulics or pneumatics to actuate movement in the arm segments. Computers allow precise, repeatable movements of the robotic arm.

Prior Selectively Compliant Articulated Robot Arm (SCARA) robots operate with 4 or fewer degrees of freedom ("DOF"). In other words, these robotic arms are designed to move along 4 or fewer axes. A typical application for a conventional robotic arm is that of pick-and-place type machine. Pick-and-place type machines are used for automation assembly, automation placing, printed circuit board manufacturing, integrated circuit pick and placing, and other automation jobs that contain small items, such as machining, measuring, testing, and welding. These robotic arms include an end-effector, also known as robotic peripheral, robotic accessory, robot or robotic tool, end of arm (EOA) tooling, or end-of-arm device. The end-effector may be an implement such as a robotic gripper, press tool, paint gun, blowtorch, deburring tool, arc welding gun, drills, etc. These end-effectors are typically placed at the end of the robotic arm and are used for uses as described above. One common end-effector is a simplified version of the hand, which can grasp and carry different objects. Such end effectors typically support maximum payloads ranging from 3 kg-20 kg (6.61-44.09 pounds).

Some conventional robots have been employed for patient positioning for such applications as external radiotherapy. One such patient position system is the Harvard Cyclotron Laboratory robotic table/chair for large fields. This design is used for a fixed horizontal proton beam treatment room based on a turntable platform, air pads, and four independently driven legs. Another patient position system is the stereotactic device "Star" for radiosurgery used at the proton line of Harvard Cyclotron Laboratory. This "Star" design is based on an air-suspension system and a double rotation of the base around a vertical axis and the patient around its own horizontal main axis.

Another patient positioning system uses a robotic chair for treatments of ocular and head targets based on a six DOF parallel link robot and a rotational platform. Another example is a table attached to a patient positioner for the gantry rooms of the Northeast Protontherapy Center at Boston. This particular design is based on a linear robot with 6 DOF. The 6 DOF of this design, however, include at least three (3) linear axes. These three linear axes facilitate only translational movements. Additionally, this design seems to only facilitate rotational movement in one DOF with respect to the movement of the attached table, and moreover this robot is attached to the floor or in a pit under the floor.

BRIEF DESCRIPTION OF THE DRAWINGS

Embodiments of the present invention are illustrated by way of example, and not by way of limitation, in the figures of the accompanying drawings and in which.

DETAILED DESCRIPTION

In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

A robotic patient positioning assembly is described for adjusting patient position during, for example, therapeutic radiation treatment using a therapeutic radiation treatment system. The robotic patient positioning assembly includes an articulated robotic arm that includes a track mount assembly to facilitate movement of a patient on a patient treatment couch (e.g., table or chair) in a three-dimensional (3D) space, as well raising and lowering the patient to high and low positions without compromising the flexibility or positioning in translational and rotational movements. The track mount assembly may be vertically mounted, for example, to a vertical side of a column.

The robotic arm can position a patient treatment couch attached to the robotic arm in five DOF, and one substantially vertical, linear DOF. The five DOF include two rotational axes for translational movements along mutually orthogonal x-, and y-horizontal coordinate axes; and three rotational axes for roll-, pitch-, and yaw-rotational movements about x-, y-, and z-axes, respectively. The one substantially vertical, linear DOF includes a substantial linear axis for translation along a substantially vertical line in a z-coordinate axis perpendicular to the horizontal, x-, and y-coordinate axes. In one embodiment, the patient treatment couch and the vertically mounted robotic arm may enable support of a patient load up to five hundred pounds (500 lbs) with a deflection of approximately zero to five millimeters (0 to 5 mm).

In another embodiment, the robotic arm includes an additional plate member attached between the shoulder assembly and the track mount assembly to provide an additional rotational DOF, totaling six rotational DOF and one substantially vertical, linear DOF. The six DOF include three rotational axes for translational movements along mutually orthogonal x-, y-, and z-coordinate axes; and three rotational axes for roll-, pitch-, and yaw-rotational movements about x-, y-, and z-axes, respectively. The one substantially vertical, linear DOF includes a substantial linear axis for translation along a substantially vertical line in a z-coordinate axis perpendicular to the horizontal, x-, and y-coordinate axes.

Figure 1:
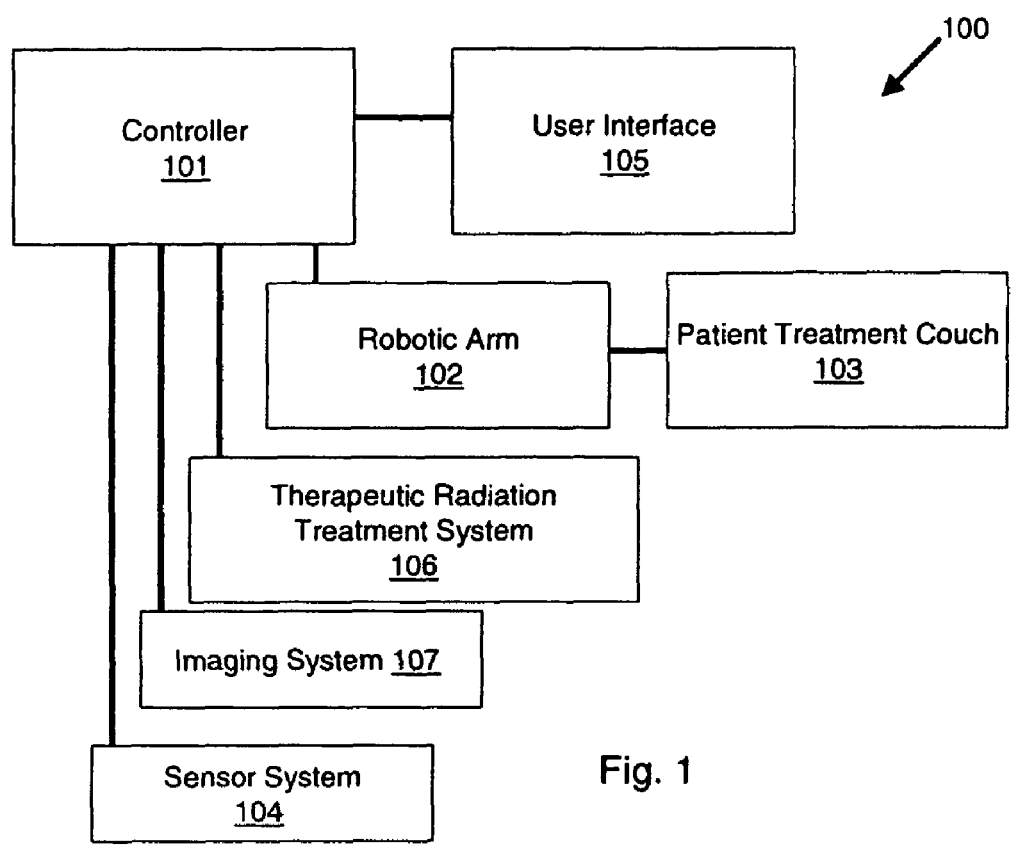
FIG. 1 illustrates a schematic block diagram of one embodiment of a robotic patient positioning assembly for therapeutic radiation treatment.

FIG. 1 illustrates a schematic block diagram of one embodiment of a robotic patient positioning assembly that adjusts a patient's position under computer control, during therapeutic radiation treatment. In this embodiment, the robotic patient positioning assembly 100 includes: 1) a patient treatment couch 103 for supporting and positioning a load, such as a patient during therapeutic radiation treatment, and 2) a robotic arm 102, which facilitates positioning of the patient treatment couch in five rotational DOF and one substantially vertical, linear DOF in a 3D workspace or operating envelop in a treatment room. The controller 101 of FIG. 1 is coupled to the robotic arm 102, sensor system 104, user interface 105, therapeutic radiation treatment system 106, and imaging system 107. The robotic arm 102 is coupled to the patient treatment couch 103.

The robotic patient positioning assembly 100 may further include a sensor system 104 for detecting the position of the patient treatment couch 103; a controller 101 for controlling the motion of the robotic arm 102 and patient treatment couch 103; a user interface unit 105, which allows a user to manually control the motion of the robotic arm 102 and the patient treatment couch 103; and a therapeutic radiation treatment system 106. The controller 101 may be operatively coupled to the sensor system 104 and the user interface unit 105 of the robotic patient positioning assembly 100 in order to calculate the position of the patient treatment couch 103 relative to the treatment room or other predefined treatment coordinate system based on the data received from the sensor system 104. The controller 101 may also operate to control the motion of the robotic patient positioning assembly 100 in a way that a treatment target within the patient's anatomy remains properly aligned with respect to a treatment beam source of a therapeutic radiation treatment system 106 throughout the treatment procedure. Controller 101 may also be used to operate the therapeutic radiation treatment system 106. In one embodiment, the therapeutic radiation treatment system 106 may be a frameless, image-guided robot-based therapeutic radiation treatment system utilizing a linear accelerator ("linac"), such as the CyberKnife® system developed by Accuray, Inc. of California. Alternatively, the therapeutic radiation treatment system 106 may be a gantry-based (isocentric) treatment system or other types of medical operation systems. The controller 101 may also communicate with the therapeutic radiation treatment system 106, receiving pre-treatment scan data representative of one or more pre-treatment scans of a treatment target within the patient. The pre-treatment scans may show the position and orientation of the target with respect to a pre-treatment coordinate system. The controller 101 may also receive from the imaging system 107 image data representative of real time or near real time images of the target. The image data may contain information regarding the real time or near real time position and orientation of the target with respect to a treatment coordinate system. The treatment coordinate system and the pre-treatment coordinate system are related by known transformation parameters.

The controller 101 may include an input module for receiving 1) pre-treatment scan data representative of pre-treatment scans of the target, and 2) real time or near real time image data representative of real time or near real time images of the target. The pre-treatment scans show the position and orientation of the target with respect to the pre-treatment coordinate system. The near real-time images, taken by the imaging system 107 under the command of the controller 101, show the position and orientation of the treatment target with respect to the treatment coordinate system. The treatment coordinate system and the pre-treatment coordinate systems are related by known transformation parameters. The controller 101 includes a TLS (target location system) processing unit that computes the position and orientation of the treatment target in the treatment coordinate system, using the pre-treatment scan data, the real time or near real time image data, and the transformation parameters between the pre-treatment coordinate system and the treatment coordinate system. The processing unit of the controller 101 may also compute the position and orientation of the iso-center of the therapeutic radiation treatment system 106.

The sensor system 104 of the robotic patient positioning assembly 100 for detecting the position of the patient treatment couch 103 may be a resolver-based sensor system. Alternatively, other sensor systems known by those skilled in the art may be used, such as an inertial sensor attached to the patient treatment couch 103 for sensing the motions of the patient treatment couch 103, or an infrared triangulation system, or a laser scanning system or an optical tracking system disposed within the treatment room for detecting the position of the patient treatment couch 103 relative to the treatment room or other treatment coordinate system, or an optical encoder.

An exemplary laser scanning system may scan the treatment room approximately 60×/sec to determine the position of the patient treatment couch 103. The laser scanning system may include devices performing a single plane scanning, or two-plane scanning, or multiple-plane scanning. Correspondingly, the controller 101 may be loaded with software adapted for receiving information from the sensor system 104 and calculating the position of the patient treatment couch 103, as well as the therapeutic radiation treatment system 106, so that the robotic patient positioning assembly 100 including the controller 101 always knows the position of the patient treatment couch 103. The controller 101 may be programmed to automatically or periodically calibrate the patient treatment couch 103 with the therapeutic radiation source of the therapeutic radiation treatment system 106. In an alternate embodiment, the sensor system 104 includes a magnetic tracking system for tracking the position of the patient treatment couch 103 relative to the treatment coordinate system. The magnetic tracking system preferably includes at least one transducer attached to the patient treatment couch 103.

The controller 101 may be adapted to detect a misalignment of the treatment target with the iso-center of the linac system caused by patient's movement by comparing the position of the treatment target with the iso-center of the linac system, and generate motion command signals for implementing corrective motions of the robotic patient positioning assembly 100 for aligning the treatment target with respect to the radiation treatment source of the therapeutic radiation treatment system 106.

In another embodiment, the corrective motions of the robotic patient positioning assembly 100 may accommodate for various motions, such as respiratory motion; cardiac pumping motion of the patient's heart; sneezing, coughing, or hiccupping; and muscular shifting of one or more anatomical members of the patient.

In another embodiment, the robotic patient positioning assembly 100 including the controller 101 may be adapted to detect and accommodate changes in tumor geometry that may be caused by tissue deformation by comparing the real time or near real time image with the pre-treatment image and repositioning the patient using the patient treatment couch 103 and/or the radiation source of the therapeutic radiation treatment system 106 (in a robot-based therapeutic radiation treatment system), or adjusting the positions of the patient treatment couch 103 and the radiation source of the therapeutic radiation treatment system 106 to correspond to the treatment plan.

The controller 101 includes software for establishing and maintaining a reliable communication interface with the patient treatment couch 103. The software uses the interface specifications developed for the patient treatment couch 103. The controller 101 further includes software for converting the patient position and orientation information from the imaging system 107 to appropriate units of movement in the degrees of freedom of motion capability of the patient treatment couch 103. The controller 101 may include software for providing a user interface unit 105 to the therapeutic radiation treatment system user control console, to monitor and initiate the motion of the robotic patient positioning assembly 100 for positioning the patient. The controller 100 may also include software for detecting, reporting, and handling errors in communication or software control of the patient treatment couch 103.

The controller 101 may include at least one user interface unit, such as user interface unit 105, for enabling the user to interactively control the motions or corrective motions of the robotic patient positioning assembly 100, by implementing one or more user-selectable functions. In one embodiment, the user interface unit 105 may be a handheld user interface unit or remote control unit. Alternatively, the user interface unit 105 may be a graphical user interface (GUI).

The communication links between the controller 101 and other components of the robotic patient positioning assembly 100 (e.g., the robotic arm 102, patient treatment couch 103, sensor system 104, user interface 105, therapeutic radiation treatment system 106, and imaging system 107) may be wired links or wireless links, with a bandwidth necessary for maintaining reliable and timely communications.

In one embodiment, the therapeutic radiation treatment system 106 may be a radiosurgery system, such as the CyberKnife® radiosurgery system. The radiosurgery system may include a robot, having an articulated robotic arm; a therapeutic radiation source, mounted at a distal end of the articulated robotic arm, for selectively emitting therapeutic radiation; an x-ray imaging system 107; and a controller. In one embodiment, the therapeutic radiation source may be an x-ray linac. The x-ray imaging system 107 generates image data representative of one or more real time or near real time images of the target. The x-ray imaging system 107 may include a pair of diagnostic x-ray sources, and a pair of x-ray image detectors 408 (or cameras), each detector located opposite an associated x-ray source. The patient treatment couch 103 (or treatment table) supports the patient during treatment, and may be positioned between the two x-ray cameras and their respective diagnostic x-ray sources of the imaging system 107.

The imaging system 107 generates, in real time or near real time, x-ray images showing the position and orientation of the target in a treatment coordinate frame. The controller 101 may contain treatment planning and delivery software, which may be responsive to pre-treatment scan data CT (and/or MRI data, PET data, ultrasound scan data, and/or fluoroscopy imaging data) and user input, to generate a treatment plan consisting of a succession of desired beam paths, each having an associated dose rate and duration at each of a fixed set of treatment positions or nodes. In response to the controller's directions, the robotic arm moves and orients the x-ray linac, successively and sequentially through each of the nodes, while the x-ray linac delivers the required dose as directed by the controller. The pre-treatment scan data may include, for example, CT scan data, MRI scan data, PET scan data, ultrasound scan data, and/or fluoroscopy imaging data.

Prior to performing a treatment on a patient therapeutic radiation treatment system 106, the patient's position and orientation within the frame of reference established by imaging system 107 must be adjusted to match the position and orientation that the patient had within the frame of reference of the CT (or MRI or PET or fluoroscopy) scanner that provided the images used for planning the treatment. In one exemplary embodiment, this alignment may be performed to within tenths of a millimeter and tenths of a degree for all five or six rotational degrees of freedom and the one substantially vertical, linear degree of freedom.

Although the robotic arm 102 and patient treatment couch 103 may be described herein in relation to an image-guided robot-based therapeutic radiation treatment system (and, in particular, the CyberKnife® system), the robotic arm 102 and patient treatment couch 103 may also be used with the other types of systems such as gantry-based (iso-centric) treatment systems. It should also be appreciated that the robotic patient positioning assembly 100 may alternatively be used for other medical applications, for example, as an operating room (OR) table, or as a supporting device in CT scanning or in MRI process, and the like.

Figure 2A:
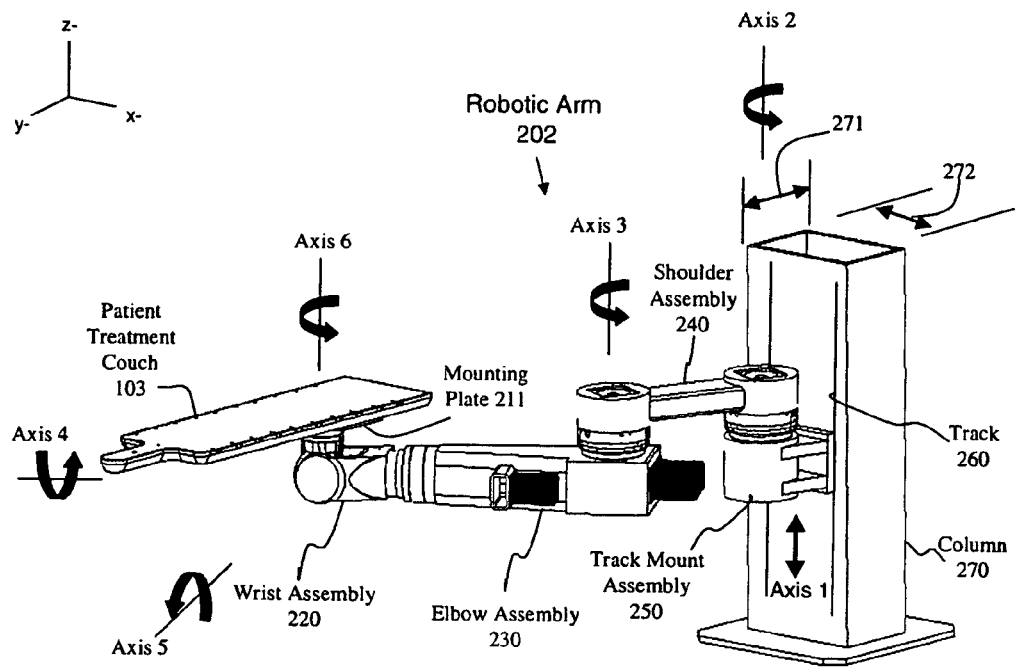
FIG. 2A illustrates one embodiment of a robotic patient positioning assembly including a robotic arm having five rotational degrees of freedom and one substantially vertical, linear degree of freedom.

FIG. 2A illustrates one embodiment of a robotic patient positioning assembly including a robotic arm having five rotational degrees of freedom and one substantially vertical, linear degree of freedom. The robotic patient positioning assembly of FIG. 2A includes a robotic arm 202 having a wrist assembly 220, an elbow assembly 230, a shoulder assembly 240, a track mount assembly 250, and a track 260; a patient treatment couch 103; and a column 270. Patient treatment couch 103 may be rotatably attached to the wrist assembly 220, which includes a tool-yaw joint, a tool-pitch joint, and a tool-roll joint. The tool-yaw joint of wrist assembly 220 may be coupled to mounting plate 211, which may be attached to the bottom of the patient treatment couch 103. The tool-yaw joint of wrist assembly 220 facilitates rotational movement of the patient treatment couch 103 in a yaw-rotation along the z-axis, axis 6 of FIG. 2A. The tool-pitch joint may be coupled to the tool-yaw joint and facilitates rotational movement of the patient treatment couch 103 in a pitch-rotation along the y-axis, axis 5 of FIG. 2A. The tool-roll joints may be coupled to the tool-pitch joint and facilitates rotational movement of the patient treatment couch 103 in a roll-rotation along the x-axis, axis 4 of FIG. 2A.

The elbow assembly 230 may be coupled to the tool-roll joint of wrist assembly 220. The elbow assembly 230 may include three drive shafts and three motors. In one embodiment, the motors discussed herein may be step motors. Alternatively, the motors may be servo motors or other motors known by those of ordinary skill in the art. The first drive shaft may be coupled to the tool-yaw joint and the first motor. The first motor and drive shaft drive rotational movement of patient treatment couch 103 along the yaw axis, axis 6. The second drive shaft may be coupled to the tool-pitch joint and the second motor. The second motor and drive shaft drive rotational movement of the patient treatment couch 103 along the pitch axis, axis 5. The third drive shaft may be coupled to the tool-roll joint and the third motor. The third motor and drive shaft drive rotational movement of the patient treatment couch 103 along the roll axis, axis 4. In one exemplary embodiment, the elbow assembly 230 is ten inches (10") in diameter at the distal end that connects to the tool-roll joint of the wrist assembly 220. Alternatively, the elbow assembly 230 may have a diameter being approximately in a range of three to twenty inches (3"-20"). Alternatively, the elbow assembly 230 may have another shape than circular, for example, rectangular, oval, or other known shapes, and the elbow assembly 230 may have a minimum measurement of its cross section between three (3") to twenty (20") inches.

The shoulder assembly 240 may be coupled to the elbow assembly 230 by an elbow joint and to the track mount assembly 250 by a shoulder joint. The elbow joint includes an elbow gearbox, which may be configured to drive rotational movement of the elbow assembly 230 of the robotic arm 202 in a rotational axis, axis 3 of FIG. 2A. The shoulder joint includes a shoulder gearbox, which may be configured to drive rotational movement of the shoulder assembly 240 of the robotic arm 202 in a rotational axis, axis 2 of FIG. 2A. The elbow and shoulder gearboxes of the shoulder and elbow assemblies 230 and 240 facilitate translational movement of the patient treatment couch 103 in a two-dimensional horizontal plane, for example, in the (x-, y-) plane parallel with the floor. In one embodiment, the elbow and shoulder gearboxes have approximately a two hundred to one gear reduction ratio (200:1). The 200:1 gear reduction ratio of the elbow and shoulder gearboxes may enable support of a patient load up to five hundred pounds within a deflection error 261 on the patient treatment couch 103, being approximately in a range of zero to sixty millimeters (0 to 60 mm). In one exemplary embodiment, the deflection error 261 is approximately zero to five millimeters (0 to 5 mm). Alternatively, the gear reduction ratios may have a range of approximately ten to one gear reduction ratio (10:1) to approximately six hundred to one gear reduction ratio (600:1). It should be noted that the structure described herein when referring to supporting a patient load up to five hundred pounds (500 lbs) may support four times (4x) the weight of the patient load in order to comply with safety standards. Further, although illustrated using a robotic arm having five rotational degrees of freedom and one substantially vertical, linear degree of freedom, deflection error 261 of FIG. 2F applies to the other embodiments of the robotic arm having six rotational degrees of freedom and one substantially vertical, linear degree of freedom described herein.

In one embodiment, the controller 101, the shoulder and elbow gearboxes of the robotic arm 202, the track mount assembly 250, and the wrist assembly 220, may include components manufactured by KUKA Roboter GmbH of Germany.

The track mount assembly 250 may be coupled to a track 260 and to the shoulder joint of the shoulder assembly 240. The track mount assembly 250 and track 260 facilitate translational movement of the patient treatment couch 103 in a substantially vertical, linear axis, axis 1 of FIG. 2A. The substantially vertical, linear axis (z-) may be substantially perpendicular to the two dimensional horizontal plane (x-, y-). In one embodiment, the track may be vertically oriented, for example, vertically mounted to a vertical side of column 270. The column 270 may be secured or mounted to the floor of the treatment room during therapeutic radiation treatment or below the floor in a pit. In another embodiment, column 270 may be secured or mounted to the ceiling of the treatment room during therapeutic radiation treatment. Alternatively, the track 260 may be vertically mounted to other structures known to those skilled in the art, such as a wall, pedestal, block, or base structure. Column 270 includes a column depth 271, and a column width 272. In one embodiment, the column depth 271 is at least approximately ten inches (10") and the column width 272 is at least approximately fifteen inches (15"). In one exemplary embodiment, the column depth 271 is approximately seventeen inches (17") and the column width 272 is approximately twenty-two inches (22"). In one embodiment, the column 270 has at least a principal moment of inertia about the x-axis of approximately 800 $in^4$. In one exemplary embodiment, the principal moment of inertial about the x-axis is approximately 1200 $in^4$.

The above mentioned arrangement of the wrist assembly 220, elbow assembly 230, shoulder assembly 240, track mount assembly 250, and track 260 facilitate the positioning of the patient treatment couch 103 using five rotational degrees of freedom and one translational substantially vertical, linear degree of freedom. The five rotational and one translational substantially vertical, linear DOF of the robotic arm 202 of the robotic patient positioning assembly 100 may position a patient on the patient treatment couch 103 in substantially any place in a desired treatment area, such as a workspace within the mechanical range of motion of the robotic arm 202. The robotic arm 202 may position the patient treatment couch 103 to have a tool center position (TCP) or iso-center in multiple locations within the workspace or treatment area. The robotic arm 202 may also provide loading/unloading positions for a particular patient, as discussed below. The robotic arm 102 may be configured to facilitate motion of the patient treatment couch 103 along five rotational DOF and one substantially vertical, linear DOF. In one exemplary embodiment, the five DOF includes two rotational axes for translational movements along mutually orthogonal, horizontal coordinate axes (x-, and y-); and three rotational axes for roll-, pitch-, and yaw-rotational movements about x-, y-, and z-axes, respectively. The one substantially vertical, linear DOF includes a substantial linear axis for translational movement along a substantially vertical line in a coordinate axis (z-) substantially perpendicular to the horizontal coordinate axes (x-, and y-).

In one embodiment, the robotic arm 202 includes one or more patient treatment couch motion actuators for moving the patient treatment couch 103, in accordance with directions from the controller 101. A table interface module allows the patient treatment couch 103 to interface with the sensor system 104, the actuators of the robotic arm 102, the controller 101, the therapeutic radiation treatment system 106, and the user interface unit 105. The electronics module may independently check patient treatment couch positions against a model of surrounding obstructions to ensure that the patient treatment couch 103 does not collide with obstacles during motion of the robotic patient positioning assembly 100.

In the illustrated embodiment of FIG. 2A, the patient treatment couch 103 may be a treatment table, although in other embodiments, other types of support devices (such as a table, chair or bench) may be used.

Figure 2B:
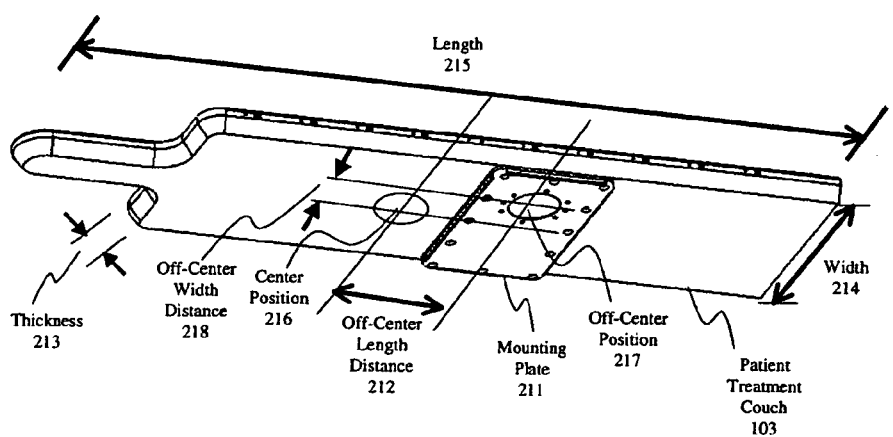
FIG. 2B illustrates one embodiment of a patient treatment couch including a mounting plate.

FIG. 2B illustrates one embodiment of a patient treatment couch including a mounting plate. Mounting plate 211 is coupled to the patient treatment couch 103. In one embodiment, the mounting plate 211 may be attached to the patient treatment couch 103 at an off-center position or pivot point. In one embodiment, the length 215 of the patient treatment couch 103 may be approximately in a range of forty-eight inches to one hundred forty-five inches (48"-145"). The width 214 of the patient treatment couch 103 may be approximately in a range of ten inches and forty-five inches (10"-45"). In one exemplary embodiment, length 215 is approximately 78 inches and the width 214 is approximately twenty inches (20").

In one embodiment, the off-center position 217 may be approximately in a range of fifty to seventy-five inches (50"-75") from one side of the patient treatment couch 103 (e.g., side that includes the patient head rest) with respect to the length 215 of the patient treatment couch 103. In one exemplary embodiment, the off-center position 217 is fifty inches (50") from one side of the patient treatment couch 103 with respect to the length 215 of the patient treatment couch 103. In another embodiment, the off-center position 217 is an off-center length distance 212 and an off-center width distance 218 from the center position 216 of the patient treatment couch 103. In one embodiment, the off-center length distance 212 may be approximately in a range of zero to ninety percent (0-90%) of a distance to one side of the patient treatment couch 103 from the center position 216 with respect to the length 215 and the off-center width distance 218 may be approximately in a range of zero to ninety percent (0-90%) of a distance to one side of the patient treatment couch 103 from the center position 216 with respect to the width 214. In an exemplary embodiment, the off-center position 217 is approximately twenty-one inches (21") from a center position 216 with respect to a length 215 of the patient treatment couch 103 and approximately four inches (4") from the center position 216 with respect to a width 214 of the patient treatment couch 103. Or in other words, the off-center length distance 212 is twenty-one inches (21") and the off-center width distance 218 is 4 inches (4"). In another embodiment, the off-center position 217 may be expressed in terms of percentages, for example, the off-center position 217 may be located within approximately 50-85% with respect to the length 215 of the patient treatment couch 103 and within approximately 0-50% with respect to the width 214 of the patient treatment couch 103. Alternatively, the mounting plate 211 may be coupled to the patient treatment couch 103 in the center position 216 with respect to the length 215 and the width 214 of the patient treatment couch 103.

The patient treatment couch 103 in one embodiment may have a thickness 213 being approximately in a range of 0.75 inches to 3 inches. In one exemplary embodiment, the patient treatment couch 103 has a thickness 213 of approximately 2.25 inches. In another exemplary embodiment, the patient treatment couch 103 has a thickness 213 of approximately 2.25 inches, a length 215 of approximately 77 inches, and a width 214 of approximately 20 inches.

Figure 2C:
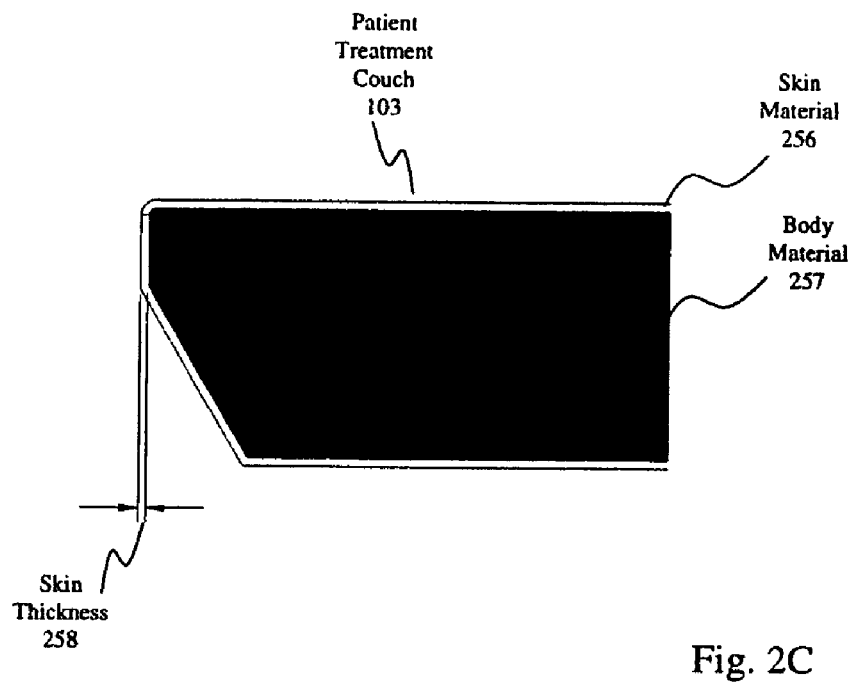
FIG. 2C illustrates a cross sectional view of one embodiment of a patient treatment couch.

FIG. 2C illustrates a cross sectional view of one embodiment of a patient treatment couch. Patient treatment couch 103 may be made of radiolucent material. In one embodiment, the patient treatment couch 103 includes a skin material 256 and a body material 257. In one exemplary embodiment, the skin material 256 is carbon fiber and the body material 257 is foam. Alternatively, other radiolucent material may be used for the skin and body materials. In one embodiment, the skin material 256 includes a skin thickness 258. The skin thickness 258 may be approximately in a range of thickness of 0.02 to 0.12 inches. In one exemplary embodiment, the skin thickness may be approximately 0.058 inches.

Figure 2D:
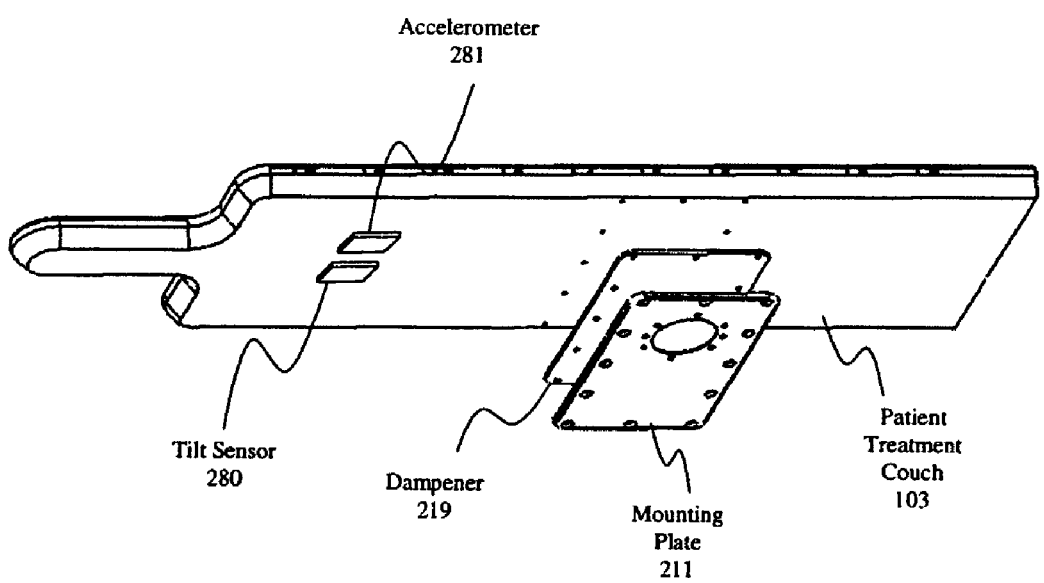
FIG. 2D illustrates one embodiment of a patient treatment couch including a mounting plate, tilt sensor, and a dampener.

FIG. 2D illustrates one embodiment of a patient treatment couch including a mounting plate, tilt sensor, accelerometer, and a dampener. In this embodiment, a dampener 219 is coupled to the mounting plate 211 and the patient treatment couch 103. The dampener 219 may include dampening material, such as, rubber or plastic. Alternatively dampener 219 may be another device known in the art to reduce or dampen vibrations, such as, a spring type element.

Tilt sensor 280 may be mounted to the patient treatment couch 103. Tilt sensor 280 may be a dual-axis tilt sensor that detects the angle of the patient treatment couch 103. The tilt sensor 280 may be coupled to the controller 101 and may be configured to send information regarding the tilt of the patient treatment couch 103, such as the angle measurement for one or more axis. The tilt sensor 280 may prevent the patient from falling off of the patient treatment couch 103 during treatment. The tilt sensor 280 may also allow the patient to feel safe from falling off the patient treatment couch 103. The tilt sensor 280 allows the patient treatment couch 103 to operate without rails to prevent the patient from falling off or being uncomfortable during treatment. In one embodiment, tilt sensor 280 may be a single axis tilt sensor and one or more tilt sensors may be used to detect tilt of the patient treatment couch 103 in the roll and pitch rotations. In another embodiment, the tilt sensor 280 may be a dual axis tilt sensor, which detects and sends information (e.g., angle measurements) to the controller 101 regarding the tilt angle of both the pitch and roll rotations of the patient treatment couch 103. Alternatively, other tilt sensors known to those of ordinary skill in the art may be used, such as, a tri-axis tilt sensor. The tilt sensor 280 may be configured to detect when the roll and/or pitch angle of the patient treatment couch 103 reaches a pre-configured angle and to halt motion of the patient treatment couch 103 so as to not exceed that pre-configured angle to prevent the patient from falling off. In one embodiment, the pre-configured angle may be approximately in a range of six to nine degrees (6-9°). In one exemplary embodiment, the pre-configured angle is seven degrees (7°). Alternatively, other specific angles may be used to prevent motion of the patient treatment couch 103 to exceed pre-configured angles during its movement in the roll or pitch axes. In one embodiment, the tilt sensor 280 may include components manufactured by Crossbow Inc., of San Jose, Calif.

Accelerometer 281 may be mounted to the patient treatment couch 103. Accelerometer 281 may detect the acceleration of the patient treatment couch 103. The accelerometer 281 may be coupled to the controller 101 and may be configured to send information regarding the acceleration of the patient treatment couch 103. The accelerometer may prevent the patient from falling off of the patient treatment couch 103 during treatment. In one embodiment, the accelerometer 281 may include components manufactured by Crossbow Inc., of San Jose, Calif. In one embodiment, the robotic patient positioning assembly 100 may include only tilt sensor 280. Alternatively, the robotic patient positioning assembly 100 may include only accelerometer 281. It should also be noted that although not illustrated in the other figures as to not obscure the discussion of other embodiments, the dampener 219, accelerometer 281, and tilt sensor 280 may be used in other embodiments described herein.

Figure 2E:
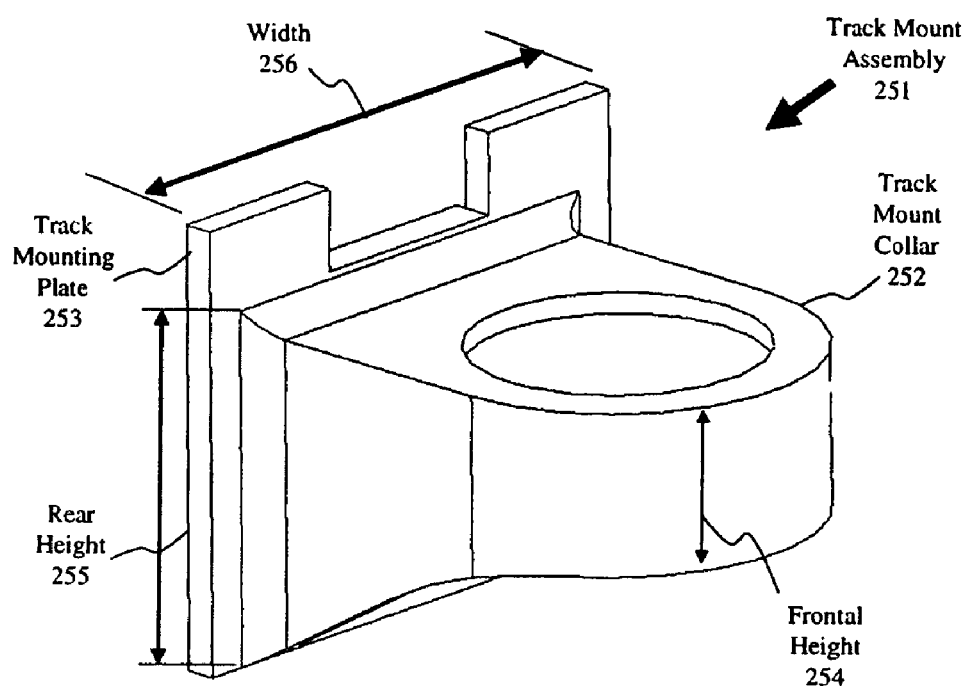
FIG. 2E illustrates one embodiment of a track mount assembly.
Figure 2F:
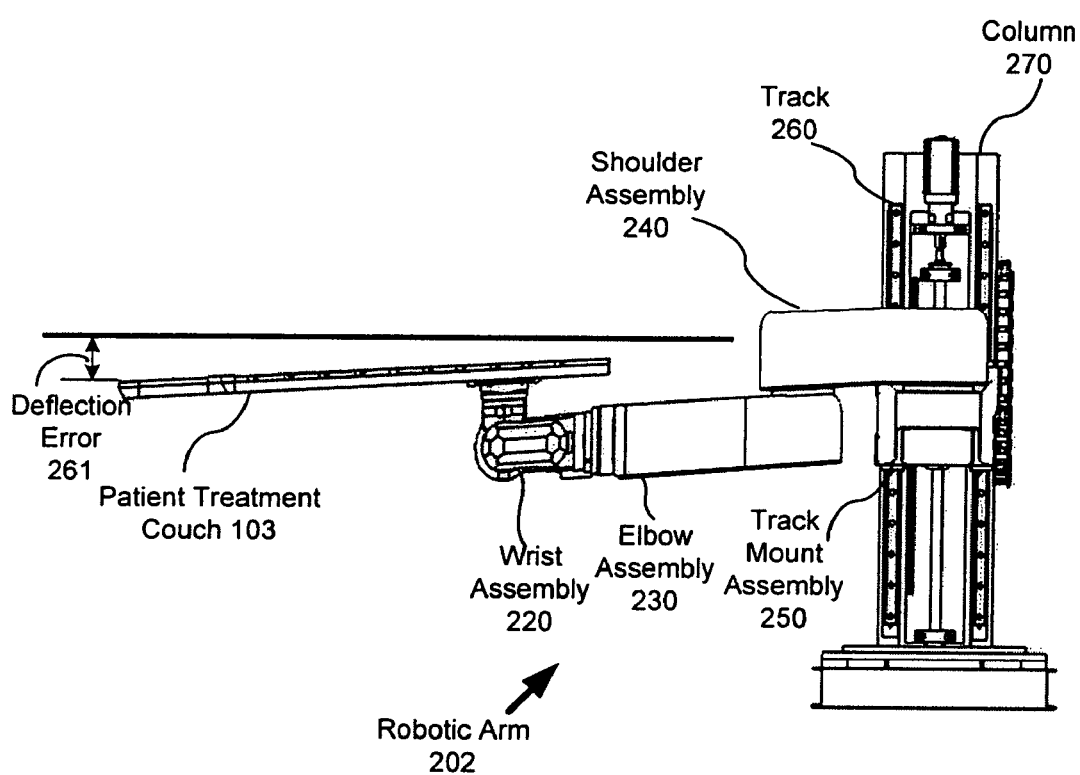
FIG. 2F illustrates one embodiment of a deflection error of a patient treatment couch and the vertically mounted robotic arm.

FIG. 2E illustrates one embodiment of a track mount assembly. Track mount assembly 251 is coupled to the track 260 and shoulder assembly 240 of FIG. 2A. It should be noted that description herein with respect to the structure and operations of the track mount assembly 250 of robotic arm 202 apply to track mount assembly 251. The track mount assembly 251 includes a track mount collar 252 and a track mount plate 253. In one embodiment, the track mount collar 252 and the track mount plate 253 may be separate components. Alternatively, the track mount collar 252 and a track mount plate 253 may be one integral piece. Track mount collar 252 includes a frontal height 254, and a rear height 255, the rear height 255 being closer to the track than the frontal height 254. In one embodiment, the rear height of the track mount collar 252 may be at least eleven inches (11"). In another embodiment, the track mount collar 252 may taper down in height from the end closest to the track mount plate 253 being greater in height than the end farthest away from the track mount plate 253. In such embodiment, the frontal height 254 at the end farthest away from the track mount plate 253 may be at least five inches (5"), while the rear height 255 at the end closest to the track mount plate 253 may be at least eleven inches (11").

In one embodiment, patient treatment couch 103 coupled to the mounting plate 211 in an off-center position 217 enables support of a patient load up to five hundred pounds within a deflection error 261 of approximately zero to five millimeters (0 to 5 mm) of the patient treatment couch 103. In another embodiment, the thickness 213 of the patient treatment couch 103 enables support of a patient load up to five hundred pounds within a deflection error 261 of approximately zero to five millimeters (0 to 5 mm) of the patient treatment couch 103. Alternatively, both the coupling of the patient treatment couch 103 to the mounting plate 211 in an off-center position 217 and the thickness 213 of the patient treatment couch enables support of a patient load up to five hundred pounds within a deflection error 261 of approximately zero to five millimeters (0 to 5 mm) of the patient treatment couch 103. It should be noted that the patient treatment couch 103 and robotic arm 202 may support more weight than five hundred pounds.

Figure 3A:
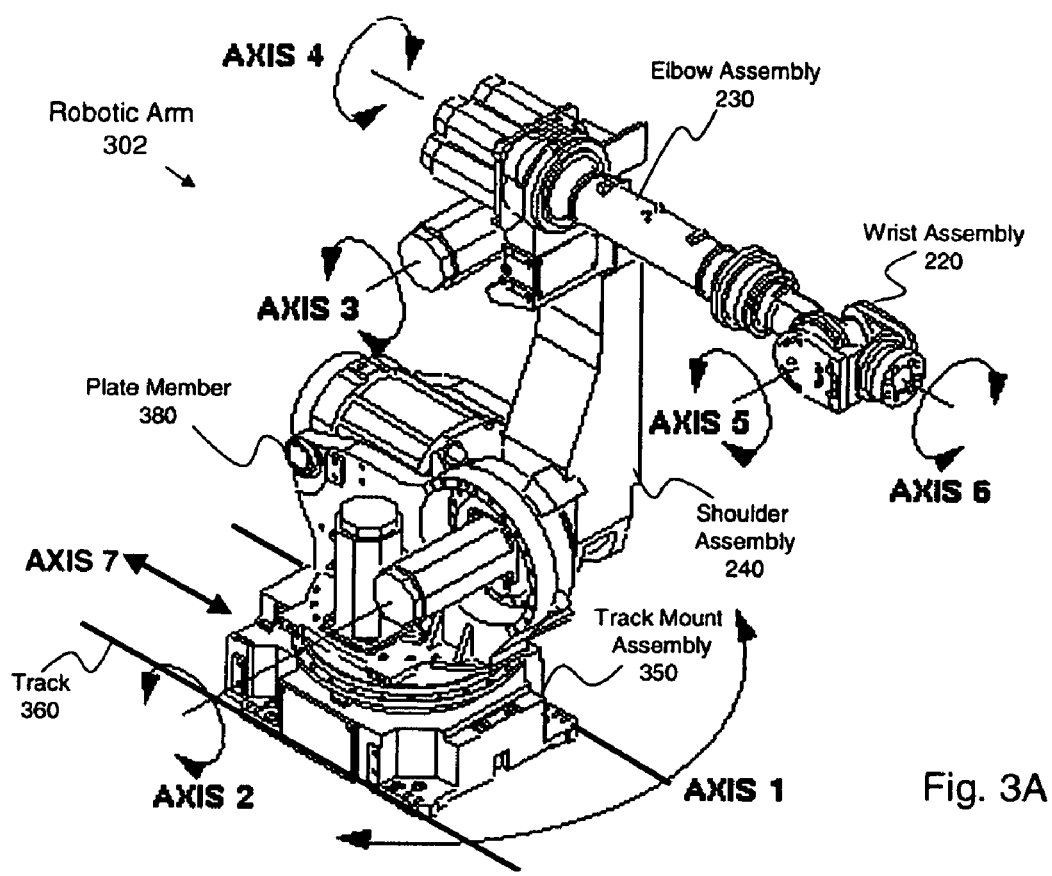
FIG. 3A illustrates one embodiment of a robotic patient positioning assembly having a robotic arm having six rotational degrees of freedom and one substantially horizontal, linear degree of freedom.

FIG. 3A illustrates one embodiment of a robotic patient positioning assembly including a robotic arm having six rotational degrees of freedom and one substantially horizontal, linear degree of freedom. As shown in FIG. 3A, the robotic patient positioning assembly includes a robotic arm 302 having a wrist assembly 220, an elbow assembly 230, a shoulder assembly 240, a plate member 380, a track mount assembly 350, and a track 360; and a patient treatment couch 103 (not illustrated in FIG. 3A). As described above, the patient treatment couch 103 may be rotatably attached to the wrist assembly 220, which includes a tool-yaw joint, a tool-pitch joint, and a tool-roll joint. The tool-yaw joint of wrist assembly 220 may be coupled to mounting plate 211, which is attached to the bottom of the patient treatment couch 103. The tool-yaw joint of wrist assembly 220 facilitates rotational movement of the patient treatment couch 103 in a yaw-rotation along a yaw axis, axis 6 of FIG. 3A. The tool-pitch joint may be coupled to the tool-yaw joint and facilitates rotational movement of the patient treatment couch 103 in a pitch-rotation along a pitch axis, axis 5 of FIG. 3A. The tool-roll joints may be coupled to the tool-pitch joint and facilitates rotational movement of the patient treatment couch 103 in a roll-rotation along a roll axis, axis 4 of FIG. 3A.

The elbow assembly 230 may be coupled to the tool-roll joint of wrist assembly 220. The elbow assembly 230 includes three drive shafts and three motors. The first drive shaft may be coupled to the tool-yaw joint and the first motor. The first motor and drive shaft drive rotational movement of patient treatment couch 103 along the yaw axis, axis 6 of FIG. 3A. The second drive shaft may be coupled to the tool-pitch joint and the second motor. The second motor and drive shaft drive rotational movement of the patient treatment couch 103 along the pitch axis, axis 5 of FIG. 3A. The third drive shaft may be coupled to the tool-roll joint and the third motor. The third motor and drive shaft drive rotational movement of the patient treatment couch 103 along the roll axis, axis 4 of FIG. 3A. In one exemplary embodiment, the elbow assembly 230 is ten inches (10") in diameter at the distal end that connects to the tool-roll joint of the wrist assembly 220. Alternatively, the elbow assembly 230 may have a diameter that is approximately three to twenty inches (3"-20"). Alternatively, the elbow assembly 230 may have another shape than circular, for example, rectangular, oval, or other known shapes, and the elbow assembly 230 may have a minimum measurement of its cross section between three (3") to twenty (20") inches. In one embodiment, the ten inch diameter of the elbow assembly coupled to the patient treatment couch 103 enables support of a patient load up to five hundred pounds within a deflection error 261 of approximately zero to five millimeters (0 to 5 mm) of the patient treatment couch 103.

The shoulder assembly 240 may be coupled to the elbow assembly 230 by an elbow joint and to the track mount assembly 350 by a shoulder joint. The elbow joint includes an elbow gearbox, which may be configured to drive rotational movement of the elbow assembly 230 of the robotic arm in a rotational axis, axis 3 of FIG. 3A. The shoulder joint includes a shoulder gearbox, which may be configured to drive rotational movement of the shoulder assembly 240 of the robotic arm in a rotational axis, axis 2 of FIG. 3A. The elbow and shoulder gearboxes of the shoulder and elbow assemblies 230 and 240 facilitate translational movement of the patient treatment couch 103 in a two-dimensional horizontal plane, for example, in the (x-, y-) plane parallel with the floor. In one embodiment, the elbow and shoulder gearboxes have approximately a two hundred to one gear reduction ratio (200:1). The 200:1 gear reduction ratio of the elbow and shoulder gearboxes may enable support of a patient load up to five hundred pounds within a deflection error 261 on the patient treatment couch 103, being approximately in a range of zero to sixty millimeters (0 to 60 mm). In one exemplary embodiment, the deflection error 261 is approximately zero to five millimeters (0 to 5 mm). Alternatively, the gear reduction ratios may range from approximately ten to one gear reduction ratio (10:1) to approximately six hundred to one gear reduction ratio (600:1).

The plate member 380 may be coupled to the shoulder joint of the shoulder assembly 240 and rotatably mounted to the track mount assembly 350. The plate member includes a gearbox, which may be configured to drive rotational movement of the plate member 380 of the robotic arm in a rotational axis, axis 1 of FIG. 3A. The gearbox of the plate member facilitates translational movement of the patient treatment couch 103 in a horizontal plane substantially parallel to the floor. In one embodiment, the gearbox of the plate member 380 has a gear reduction ratio. The gear reduction ratio of the gearbox of the plate member 380 may range from approximately two hundred and fifty to one to approximately three hundred to one (250:1 to 300:1). In one exemplary embodiment, the gear reduction ratio of the plate member gearbox is approximately 300:1.

In one embodiment, the track mount assembly 350 has similar dimensions as set forth in the discussion above with respect to FIG. 2E. Alternatively, other dimensions may be used.

In one embodiment, the wrist, elbow, and shoulder assemblies 220, 230, and 240 and the plate member 380 of the robotic arm 302 may include components manufactured by KUKA Roboter GmbH of Germany.

The track mount assembly 350 may be coupled to a track 360 and to the plate member 380. The track mount assembly 350 and track 360 facilitate translational movement of the patient treatment couch 103 in a substantially horizontal, linear axis, axis 7 of FIG. 3A. The substantially horizontal, linear axis (x-, y-) is substantially perpendicular to the two dimensional vertical plane (z-). Track 360 is coupled to the floor. In another embodiment, the track 360 may be vertically oriented, for example, vertically mounted to a vertical side of column 270. The column 270 may be secured or mounted to the floor of the treatment room during therapeutic radiation treatment or below the floor in a pit. In another embodiment, column 270 may be secured or mounted to the ceiling of the treatment room during therapeutic radiation treatment. Alternatively, the track 360 may be vertically mounted to other structures known to those skilled in the art, such as a wall, pedestal, block, or base structure.

The abovementioned arrangement of the wrist assembly 220, elbow assembly 230, shoulder assembly 240, plate member 380, track mount assembly 350, and track 360 facilitate the positioning of the patient treatment couch 103 using six rotational degrees of freedom and one translational substantially horizontal, linear degree of freedom. The six rotational and one substantially horizontal, linear DOF of the robotic arm 302 of the robotic patient positioning assembly 100 may position a patient on the patient treatment couch 103 in substantially any place in a desired treatment area, such as a workspace, within the mechanical range of motion of the robotic arm 302. The robotic arm 302 may position the patient treatment couch 103 to have a tool center position (TCP) in multiple locations within the workspace or treatment area. The robotic arm 302 may also provide loading/unloading positions for a particular patient. In one embodiment, the six DOF includes three rotational axes for translational movements along mutually orthogonal coordinate axes (x-, y-, and z-); and three rotational axes for roll-, pitch-, and yaw-rotational movements about x-, y-, and z-axes, respectively. The one substantially horizontal, linear DOF includes a substantial linear axis for translational movement along a substantially horizontal line in a coordinate axis (x-, and y-) substantially perpendicular to the vertical coordinate axes (z-).

In one embodiment, the robotic arm 302 includes one or more patient treatment couch motion actuators for moving the patient treatment couch 103, in accordance with directions from the controller 101. A table interface module allows the patient treatment couch 103 to interface with the sensor system 104, the actuators of the robotic arm 302/102, the controller 101, the therapeutic radiation treatment system 106, and the user interface unit 105. The electronics module may independently check patient treatment couch positions against a model of surrounding obstructions to ensure that the patient treatment couch 103 does not collide with obstacles during motion of the robotic patient positioning assembly 100.

As described above, the patient treatment couch 103 is capable of motion in at least five rotational degrees of freedom, namely two translational degrees of freedom (x- and y-axes) (axes 2 and 3, respectively, of FIG. 2A), three rotational degrees of freedom (yaw-, pitch-, and roll-axes) (axes 6, 5, and 4 of FIG. 2A), and one substantially vertical, linear degree of freedom (substantially vertical, linear axis) (axis 1 of FIG. 2A). Alternatively, the patient treatment couch 103 may be capable of motion in all six degrees of freedom, namely three translational degrees of freedom (x-, y-, and z-axes) (axes 3, 2 and 1, respectively, of FIG. 3A) plus three rotational degrees of freedom (roll-, pitch- and yaw-rotations) (axes 6, 5, and 4, respectively, of FIG. 3A), and one substantially vertical, linear degree of freedom (substantially vertical, linear axis) (axis 7 of FIG. 3A). The motion command signals, generated by the controller 101, may control corrective motions of the robotic patient positioning assembly 100 in the various degrees of freedom. In one embodiment, the position of the patient treatment couch 103 with respect to the treatment system 106 may be known, so that coordinated movements may be effected. In one exemplary embodiment, both the patient treatment couch 103 and the treatment system 106 can be referenced to a common (or "room") coordinate system.

Figure 3B:
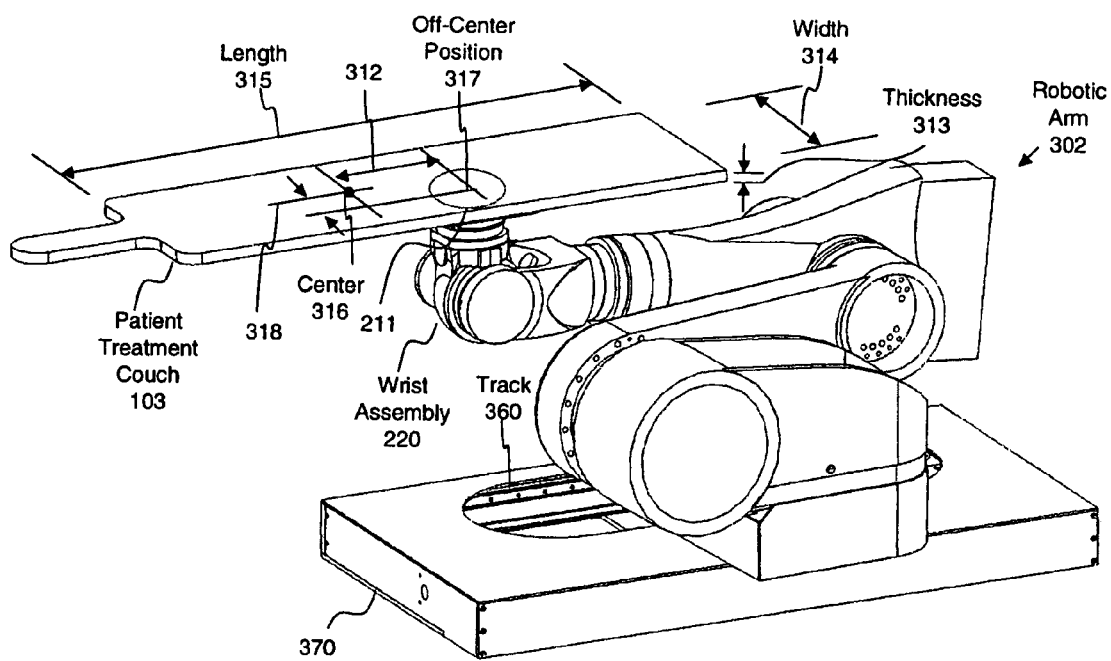
FIG. 3B illustrates one embodiment of patient treatment couch coupled to the robotic arm of FIG. 3A.

FIG. 3B illustrates one embodiment of patient treatment couch coupled to the robotic arm of FIG. 3A. Robotic arm 302 is coupled to the mounting plate 211. The robotic arm 302 is coupled to track 360. In this embodiment, track 360 is mounted to the floor and is encased in a track encasing 370. In another embodiment, the track 360 may be vertically oriented, for example, vertically mounted to a vertical side of column 270. As previously discussed, the column 270 may be secured or mounted to the floor or ceiling of the treatment room during therapeutic radiation treatment or below the floor in a pit. Alternatively, the track 360 may be vertically mounted to other structures known to those skilled in the art, such as a wall, pedestal, block, or base structure. The robotic arm 302 of FIG. 3B includes the members and assemblies that make up the robotic arm 302 of FIG. 3A, as discussed above, but these members and assemblies are not discussed with respect to FIG. 3B as to not obscure the discussion of the coupling of the robotic arm 302 and the patient treatment couch 103.

In FIG. 3B, mounting plate 211 is coupled to the patient treatment couch 103. In one embodiment, the mounting plate 211 may be attached to the patient treatment couch 103 at an off-center position or pivot point. In one embodiment, the length 315 of the patient treatment couch 103 may be approximately in a range of forty-eight to one hundred and forty five inches (48"-145"). The width 314 of the patient treatment couch 103 may be approximately in a range of ten inches and forty-five inches (10"-45"). In one exemplary embodiment, length 315 is approximately 78 inches and the width 314 is approximately twenty inches (20").

In one embodiment, the off-center position 317 may be approximately in a range of fifty to seventy-five inches (50"-75") from one side of the patient treatment couch 103 (e.g., side that includes the patient head rest) with respect to the length 315 of the patient treatment couch 103. In one exemplary embodiment, the off-center position 317 is fifty inches (50") from one side of the patient treatment couch 103 with respect to the length 315 of the patient treatment couch 103. In another embodiment, the off-center position 317 is an off-center length distance 312 and an off-center width distance 318 from the center position 316 of the patient treatment couch 103. In one embodiment, the off-center length distance 312 may be approximately in a range of zero to ninety percent (0-90%) of a distance to one side of the patient treatment couch 103 from the center position 316 with respect to the length 316 and the off-center width distance 318 may be approximately in a range of zero to ninety percent (0-90%) of a distance to one side of the patient treatment couch 103 from the center position 316 with respect to the width 314. In an exemplary embodiment, the off-center position 317 is approximately twenty-five inches (25") from a center position 316 with respect to a length 315 of the patient treatment couch 103 and approximately four inches (4") from the center position 316 with respect to a width 314 of the patient treatment couch 103. Or in other words, the off-center length distance 312 is twenty-one inches (21") and the off-center width distance 318 is four inches (4"). In another embodiment, the off-center position 317 may be expressed in terms of percentages, for example, the off-center position 317 may be located within approximately 50-85% with respect to the length 315 of the patient treatment couch 103 and within approximately 0-50% with respect to the width 314 of the patient treatment couch 103. Alternatively, the mounting plate 211 may be coupled to the patient treatment couch 103 in the center position 216 with respect to the length 215 and the width 214 of the patient treatment couch 103.

The patient treatment couch 103 in one embodiment may have a thickness 313 approximately in a range of 0.75 inches to 3 inches. In one exemplary embodiment, the patient treatment couch 103 has a thickness 313 of approximately 2.25 inches. In another exemplary embodiment, the patient treatment couch 103 has a thickness 313 of approximately 2.25 inches, a length 315 of approximately 77 inches, and a width 314 of approximately 20 inches. As described above in relation to the discussion of FIG. 2C, the patient treatment 103 may be made of radiolucent material. In one embodiment, the patient treatment couch 103 includes a skin material 256 and a body material 257. In one exemplary embodiment, the skin material 256 is carbon fiber and the body material 257 is foam. Alternatively, other radiolucent material may be used for the skin and body materials. In one embodiment, the skin material 256 includes a skin thickness 258. The skin thickness 258 may be approximately in a range of 0.02 to 0.12 inches. In one exemplary embodiment, the skin thickness may be approximately 0.058 inches.

In one embodiment, patient treatment couch 103 coupled to the mounting plate 211 in an off-center position 317 enables support of a patient load up to five hundred pounds within a deflection error 261 of approximately zero to five millimeters (0 to 5 mm) of the patient treatment couch 103. In another embodiment, the thickness 313 of the patient treatment couch 103 enables support of a patient load up to five hundred pounds within a deflection error 261 of approximately zero to five millimeters (0 to 5 mm) of the patient treatment couch 103. Alternatively, both the coupling of the patient treatment couch 103 to the mounting plate 211 in an off-center position 317 and the thickness 313 of the patient treatment couch enables support of a patient load up to five hundred pounds within a deflection error 261 of approximately zero to five millimeters (0 to 5 mm) of the patient treatment couch 103. It should be noted that the patient treatment couch 103 and robotic arm 302 may support more weight than five hundred pounds. In one embodiment, the patient treatment couch 103 and robotic arm 302 may enable support of a patient load up to approximately two thousand pounds (2000 lbs) in a static position.

Figure 4A:
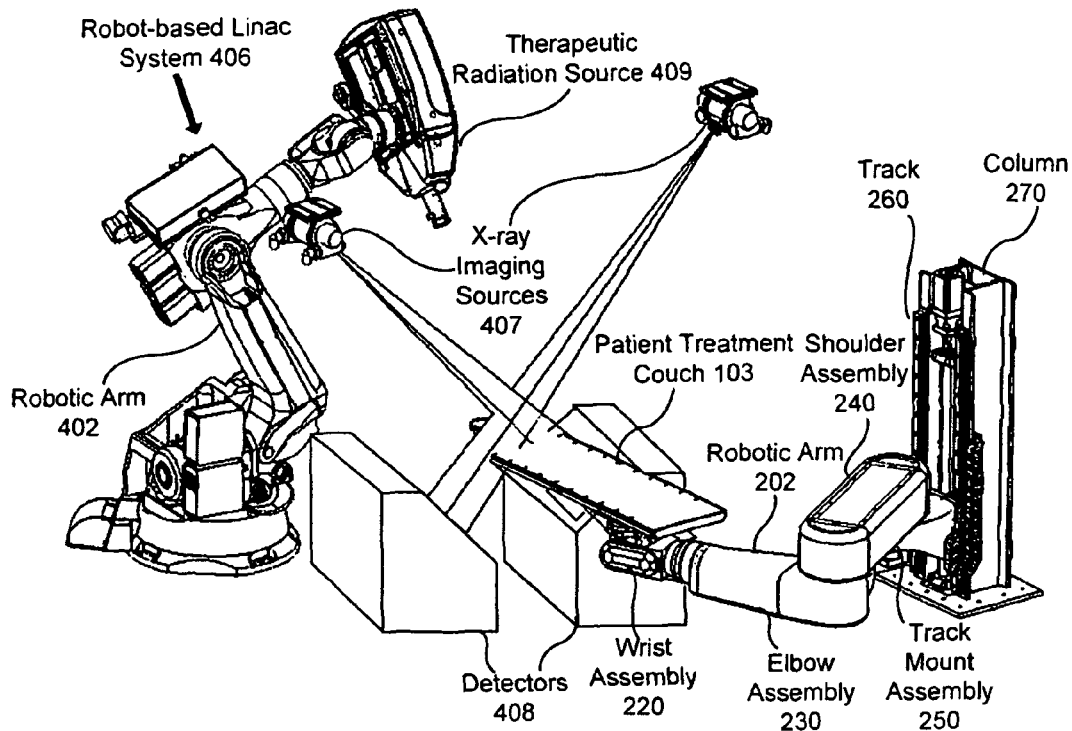
FIG. 4A illustrates one exemplary position of the robotic patient positioning assembly having five rotational degrees of freedom and one substantially vertical, linear degree of freedom together with a robot-based linear accelerator system.
Figure 4B:
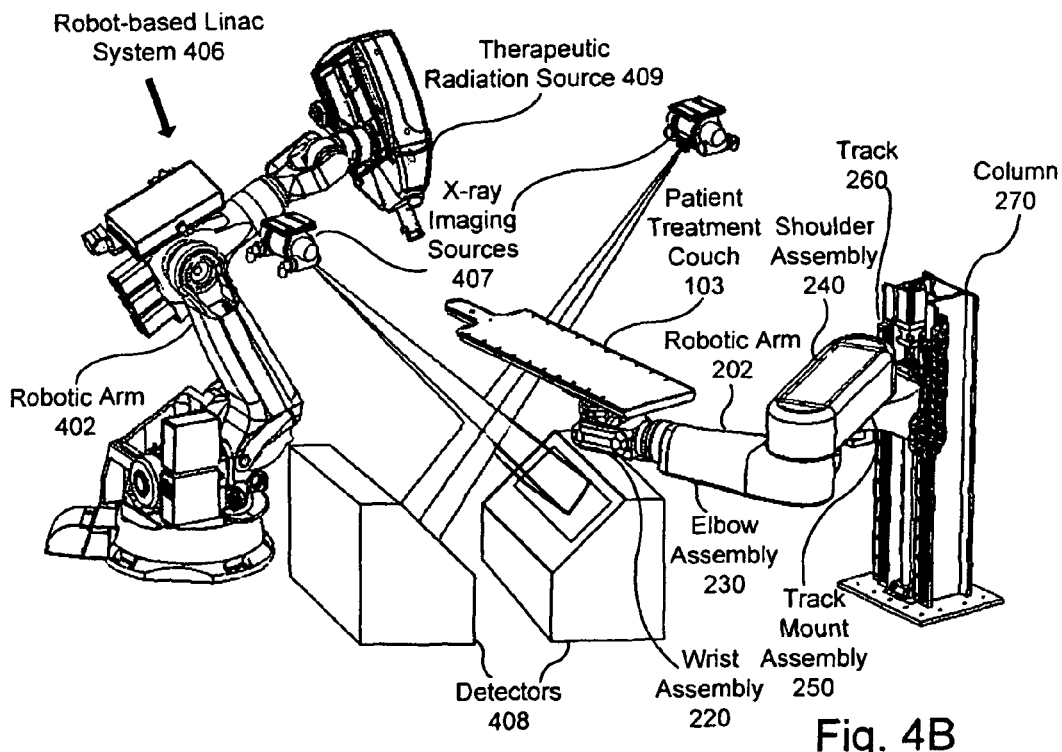
FIG. 4B illustrates another exemplary position of the robotic patient positioning assembly having five rotational degrees of freedom and one substantially vertical, linear degree of freedom together with a robot-based linear accelerator system.

FIGS. 4A and 4B illustrate exemplary positions of the robotic patient positioning assembly 100 having five rotational degrees of freedom and one substantially vertical, linear degree of freedom together with a robot-based linac system 406. The robotic patient positioning assembly 100 of FIGS. 4A and 4B includes a robotic arm 202, patient treatment couch 103, mounting plate 211, wrist assembly 220, elbow assembly 230, shoulder assembly 240, track mount assembly 250, track 260, column 270, robot-based linac system 406 having robotic arm 402, and x-ray imaging sources 407 of imaging system 107. In the illustrated embodiments, the robot-based linac system 406 may be the CyberKnife® radiosurgery system or another robot-based linac system. The robotic patient positioning assembly 100 of FIG. 4A illustrates an exemplary low position or loading/unloading position of the patient treatment couch 103 having a load (e.g., a patient). In one embodiment, this low position may be a pre-programmed position for loading/unloading a patient. The low position or loading/unloading position may be approximately in a range of sixteen to twenty-five inches (16"-25") from the floor. In this embodiment, a patient may be loaded to the patient treatment couch 103 from a wheelchair. Alternatively, the position may result from the user manually controlling the robotic arm 202 and patient treatment couch 103 by the user interface 105.

The robotic patient positioning assembly 100 of FIG. 4B illustrates an exemplary high or "TREAT" position of the patient treatment couch 103. In this exemplary embodiment, the high or "TREAT" position is higher than the low position of FIG. 4A for loading/unloading a patient. In one embodiment, the high position may be a default position before beginning treatment. This "TREAT" position may be pre-programmed in the controller 101 or alternatively, may result from manual control from the user from the user interface 105.

In one embodiment, the patient treatment couch 103 may be made of a radiolucent material so that the patient could be imaged through the patient treatment couch 103. An exemplary imaging system 107 that can be used with the robotic patient positioning assembly 100 and the robot-based linac system 406 includes two x-ray imaging sources 407, power supplies associated with each x-ray imaging source, one or two imaging detectors 408, and controller 101. The x-ray imaging sources 407 may be mounted angularly apart, for example, about 90 degrees apart, and aimed through the treatment target (e.g., tumor within the patient) toward the detector(s) 408. Alternatively, a single large detector may be used that would be illuminated by each x-ray source. In the single detector imaging system 107, the two x-ray sources 407 may be positioned apart at an angle less than 90 degrees to keep both images on the single detector surface.

The detector(s) 408 may be placed below the treatment target, e.g., on the floor, on the patient treatment couch 103, or underneath the patient treatment couch 103, and the x-ray imaging sources 407 may be positioned above the treatment target (e.g. the ceiling of the treatment room), to minimize magnification of the images and therefore the required size of the detector(s) 408. In an alternative embodiment, the positions of the x-ray imaging sources 407 and the detector(s) 408 may be reversed, e.g. the x-ray imaging sources 407 below the treatment target and the detector(s) 408 above the treatment target. In another embodiment, due to the constrained swing of the gantry of the therapeutic radiation treatment system 106, and to reduce the magnification effects, the detector(s) 408 may be arranged in a manner such that they move into position for imaging while the gantry may be positioned in a way that does not interfere with the imaging system 107, and then move out of the way during delivery of the therapeutic beam of the therapeutic radiation treatment system 106.

The detector(s) 408 may generate the image information of the patient and send it to the controller 101. The controller 101 performs all the imaging calculations to determine the patient's position with respect to the desired treatment position and generate corrections for the various degrees of freedom. The corrections could be automatically applied to the robotic patient positioning assembly 100 to automatically align the patient, and/or sent to the controller 101 to automatically adjust the patient's position relative to the therapeutic radiation source 409 of the robot-based linac system 406, and/or sent to the user interface unit 105 for a user to manually adjust the patient's position relative to the therapeutic radiation source 409 of the robot-based linac system 406.

As previously mentioned, the robotic patient positioning assembly 100 including the controller 101 may know the position of the patient treatment couch 103 through the sensor system 104 and the position of the treatment target through the real time or near real time image data, and also knows the position of the of the linac system and may generate motion command signals for implementing corrective motions of the robotic patient positioning assembly 100 for aligning the treatment target with respect to the radiation treatment sources of the therapeutic radiation treatment system 106. In one embodiment using a robot-based linac system 406 for the therapeutic radiation treatment system 106, the corrective motions of the robotic patient positioning assembly 100 may be dynamically coordinated with the motions of the treatment x-ray source of the therapeutic radiation treatment system 106 using the controller 101, in a way as to maximize the workspace available to the robot-based linac system 406. In other words, by dynamically coordinating the motions of the treatment x-ray source of the therapeutic radiation treatment system 106 using the controller 101, the available number of treatment targets increases due to the increased number of orientations and positions of the patient treatment couch 103 and the therapeutic radiation treatment system 106, which are free of obstructions, for example, by detectors 408 and/or x-ray imaging sources 407 (as shown in FIGS. 4A & 4B). In this embodiment, the robot-implemented movements of the treatment x-ray source of the robot-based linac system 406 are complemented by the corrective motions of the robotic patient positioning assembly 100, so that the relative motion between the treatment x-ray source and the patient treatment couch 103 ensures the delivery of the desired radiation pattern throughout the target region.

In one embodiment, the combination of the motions of the patient treatment couch 103 and the motions of the x-ray linac of the therapeutic radiation treatment system 106, are dynamically coordinated and controlled, so as to maximize the workspace available to the therapeutic radiation treatment system 106.

The robotic arm 202 may position the patient treatment couch 103 to have a tool center position (TCP) or treatment target in multiple locations within the workspace or treatment area. The robotic arm of the robot-based linac system 406 may also position the iso-center of the linac therapeutic radiation source 409 in multiple locations within the workspace or treatment area. The workspace or treatment area, however, may be limited by positioning restrictions, for example, obstructions caused by a possible collisions between either the patient treatment couch 103, the therapeutic radiation source 409, or their corresponding robotic arms with components of the therapeutic radiation treatment system 106, imaging system 107, and/or robotic arm 102 or obstruction of the radiation beam of the therapeutic radiation source 409 of the robot-based linac system 406 with any of these above mentioned components. For example, the x-ray imaging sources 407 may prevent the therapeutic radiation source 409 of the robot-based linac system 406 from being positioned where the x-ray imaging sources 407 are mounted because positioning it there would result in a possible collision (e.g., collision obstructions). Similarly, the therapeutic radiation source 409 of the robot-based linac system 406 may not be positioned under the patient treatment couch 103 due to the placement of the detectors 408 (e.g., collision obstructions). Another example of a positioning restriction is obstructions of the radiation beam from the therapeutic radiation source 409 due to other components, for example, the detectors 408 and/or x-ray imaging sources 407 (e.g., beam obstructions).

In one embodiment, the controller 101 may be configured to dynamically move in combination the patient treatment couch along five rotational degrees of freedom and one substantially vertical, linear degree of freedom using the robotic arm, and the robot-based linac system along at least five degrees of freedom using a robotic arm of the robot-based linac system to dynamically coordinate orientation and position of the patient treatment couch 103 and a therapeutic radiation source 409 of the robot-based linac system 406. The dynamic coordination of movement between the patient treatment couch and the therapeutic radiation source may increase a number of treatment targets within a mechanical range of motion of the robotic arm.

The controller 101 may be configured to position the patient treatment couch 103 and the robot-based linac system to create a treatment target in a previously obstructed location caused by a positioning restriction within a mechanical range of motion of the robotic arm and the robot-based linac system. In one embodiment, the previously obstructed location may be caused by an obstruction of a possible collision, for example, between either the patient treatment couch 103, therapeutic radiation source 409, or their corresponding robotic arms with the robotic arm 202, the patient treatment couch 103, the therapeutic radiation source 409, x-ray imaging sources 407, detectors 408, and/or other components of the robot-based linac system 406. Alternatively, the previously obstructed location may be caused by an obstruction of the radiation beam of the therapeutic radiation source 409 with the robotic arm 202, the patient treatment couch 103, the therapeutic radiation source 409, x-ray imaging sources 407, detectors 408, and/or other components of the robot-based linac system 406.

In one embodiment, an anti-collision model may be embedded in the controller 101 to ensure that the patient is not positioned in an orientation and/or position that might cause a possible collision between the patient treatment couch 103 including the patient's body and the linac gantry or other moving parts of the robot-based linac system 406.

Figure 4C:
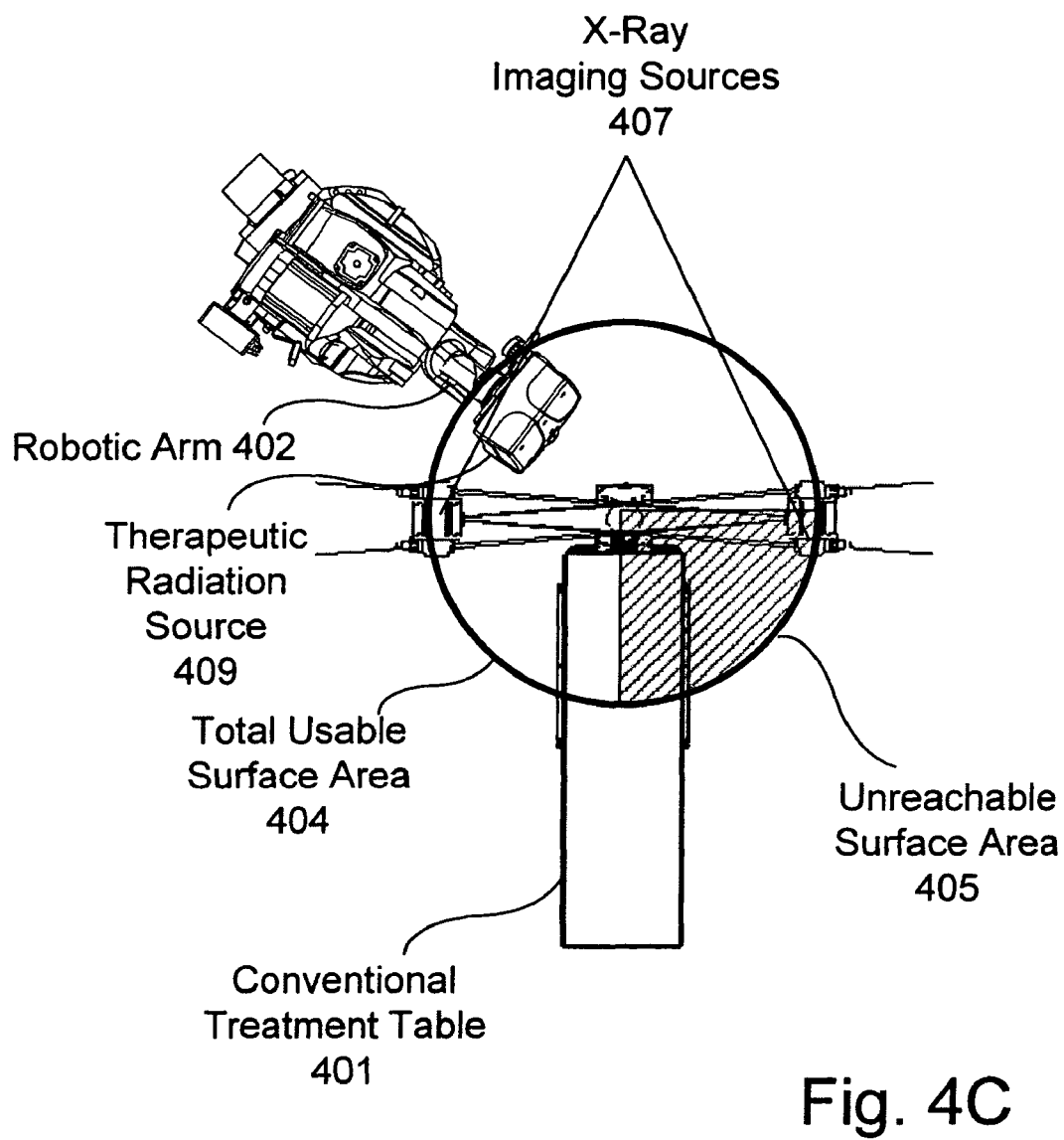
FIG. 4C illustrates a top-down view of a total usable surface area a therapeutic radiation source having a robotic arm mounted to a first side of a conventional treatment table.

FIG. 4C illustrates a top-down view of a total usable surface area a therapeutic radiation source having a robotic arm of the robot-based radiosurgery system mounted to a first side of a conventional treatment table. In this embodiment, therapeutic radiation source 409 is coupled to a robot-based linac system 406, as described above with respect to FIGS. 4A and 4B. The robot-based linac system 406 is mounted to the floor on one side of a conventional treatment table 401. Conventional treatment couch 401 is a floor mounted treatment table. As described above, the therapeutic radiation source 409 may be positioned using the robotic arm 402 of the linac system 406 (e.g., articulated robotic arm) in a three-dimensional workspace within the mechanical range of motion of the robotic arm 402. The therapeutic radiation source 409 may be positioned to be a certain distance from the treatment target within the patient on the conventional treatment table 401. The certain distance between the radiation source 409 and the treatment target of the patient is the source axis distance (SAD). Since the robot-based radiation source 409 may be positioned and oriented within the 3-D workspace using the robotic arm 402 of the robot-based linac system 406, the radiation source 409 has a total usable surface area 404, which may be dependant upon the SAD. In one embodiment, if the SAD is a fixed number, the total usable surface area 404 would have approximate spherical shape. Alternatively, other usable surface areas may be used of different shapes that have been obtained by varying the SAD. The total usable surface area 404 may represent the positions or nodes in which the radiation source 409 (e.g., x-ray linac) may be positioned to emit therapeutic radiation to the treatment target within the patient. The total usable surface area 404 may be limited by positioning restrictions as described above.

In one embodiment, the positioning restriction may be caused by a treatment table or couch. In one exemplary embodiment, the position restriction may cause an unreachable surface area 404 due to the obstruction of the floor mounted conventional treatment table and the floor mounted robot-based linac system 406. Alternatively, other obstructions may cause the radiation source 409 to have unreachable surface areas. In one embodiment, the unreachable surface area 404 may be caused by the robot-based linac system 406 being mounted to one side of the conventional treatment table 401, as illustrated in FIG. 4C. FIG. 4C includes a two-dimensional circular shape of the total usable surface area 404 and the unreachable surface area 405. It should be noted that although represented as a two-dimensional circular shape in FIG. 4C, the total usable surface area 404 may be the surface area of an approximate spherical shape. Alternatively, other usable surface areas may be used of different shapes that have been obtained by varying the SAD.

Figure 4D:
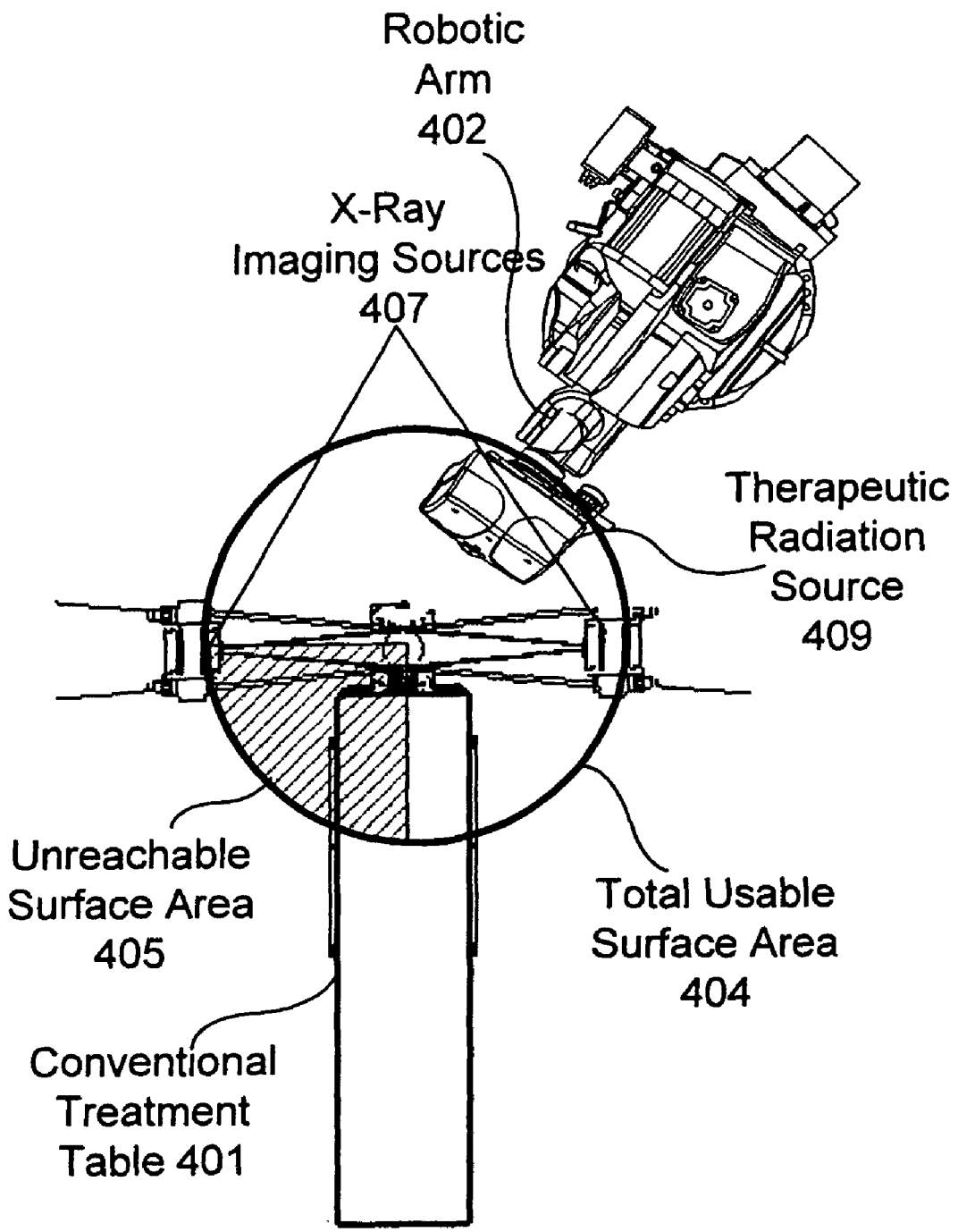
FIG. 4D illustrates a top-down view of the total usable surface area of the therapeutic radiation source having the robotic arm mounted to a second side of the conventional treatment table.

It should be noted that the unreachable area 404 can not be cured by merely mounting the robotic arm of the robot-based linac system 406 on the opposite side of the conventional treatment table 401, as illustrated in FIG. 4D. FIG. 4D illustrates a top-down view of the total usable surface area 404 of the therapeutic radiation source 409 having the robotic arm of the robot-based linac system 406 mounted to a second side of the conventional treatment table 401. In this embodiment, the unreachable surface area 405 remains due to the obstruction of the conventional treatment table 401 and the robotic arm of the robot-based linac system 406. In other words, merely mounting the robot-based radiosurgery system on another side does not overcome the positioning restriction due to the obstruction causing the unreachable area 405.

Figure 4E:
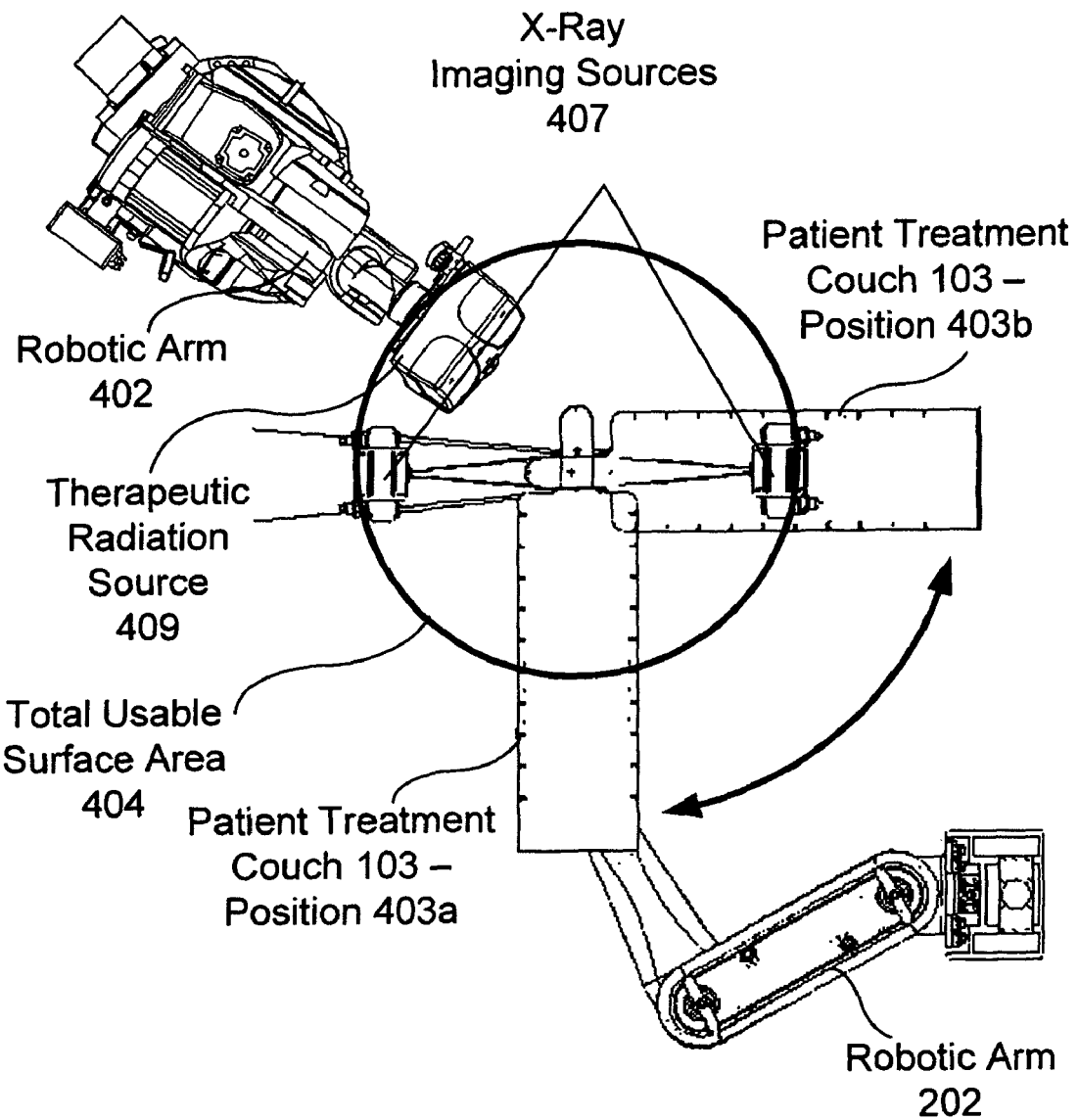
FIG. 4E illustrates a top-down view of a total usable surface area of one embodiment of a therapeutic radiation source and a patient treatment couch.

FIG. 4E illustrates a top-down view of a total usable surface area of one embodiment of a therapeutic radiation source and a patient treatment couch. In this embodiment, therapeutic radiation source 409 is coupled to a robot-based linear accelerator system 406 as described above with respect to FIGS. 4A and 4B. In this embodiment, therapeutic radiation source 409 is coupled to a robot-based linac system 406, as described above with respect to FIGS. 4A and 4B. The robot-based linac system 406 is mounted to the floor on one side of patient treatment couch 103 in position 403a. Alternatively, the robot-based linac system 406 may be mounted to the floor on the opposite side of patient treatment couch 103. Patient treatment couch 103 is coupled to robotic arm 202. The details of patient treatment couch 103 and robotic arm 202 have been described herein, and are not repeated here as to not obscure the discussion of increasing the total usable surface area 404. In this embodiment, patient treatment couch 103 and robotic arm 202 are vertically mounted. Alternatively, a floor or ceiling mounted robotic arm may be used. As described above, the therapeutic radiation source 409 may be positioned using the robotic arm 402 of the linac system 406 (e.g., articulated robotic arm) in a three-dimensional workspace within the mechanical range of motion of the robotic arm 402. The therapeutic radiation source 409 may be positioned to be a certain distance, the SAD, from the treatment target of the patient on the patient treatment couch 103. Since the robot-based radiation source 409 may be positioned and oriented within the 3-D workspace using the robotic arm 402 of the robot-based linac system 406, the radiation source 409 has a total usable surface area 404, which may be dependant upon the SAD. In one embodiment, if the SAD is a fixed number, the total usable surface area 404 would have approximate spherical shape. Alternatively, other usable surface areas may be used of different shapes that have been obtained by varying the SAD.

The total usable surface area 404 may represent the positions or nodes in which the radiation source 409 (e.g., x-ray linac) may be positioned to emit therapeutic radiation to the treatment target of the patient. The total usable surface area 404 may be limited by positioning restrictions as described above.

As described above, the positioning restriction may be caused by treatment table or couch. In this embodiment, however, the patient treatment couch 103 and the robotic arm 202 may be positioned to eliminate the unreachable area 405 as described and illustrated with respect to FIGS. 4C and 4D. FIG. 4E illustrates the new position of the patient treatment couch 103 as patient treatment couch 403b. In this embodiment, the position of the patient treatment couch 103 is shifted from position 403a to 403b. In other words, the patient treatment couch 103 coupled to the robotic arm 202 may increase the total usable surface area 404 that the therapeutic radiation source 409 may be positioned for emitting therapeutic radiation to the treatment target of the patient. Alternatively, other movements may be used to eliminate the unreachable surface area and to increase the total usable surface area 404 of FIG. 4E.

FIG. 4E includes a two-dimensional circular shape of the total usable surface area 404. It should be noted that although represented as a two-dimensional circular shape in FIG. 4C, the total usable surface area 404 may be the surface area of an approximate spherical shape. Alternatively, other usable surface areas may be used of different shapes that have been obtained by varying the SAD.

In another embodiment, the obstruction may be caused by the ground; thus, when using a conventional treatment table 401, the obstruction creates an unreachable surface area on a bottom portion of an approximately spherical usable area. Using a vertically mounted robotic arm 202 and patient treatment couch 103 the patient treatment couch 103 may be raised up from the floor from a first position to a second higher position, eliminating the unreachable surface area and increasing the total usable surface area. Alternatively, other unreachable surface areas may be overcome by coordinating the movement of the robotic arm 202 and the patient treatment couch 103, such as, for example, obstructions due to the detectors 408, and x-ray imaging sources 407.

Figure 4F:
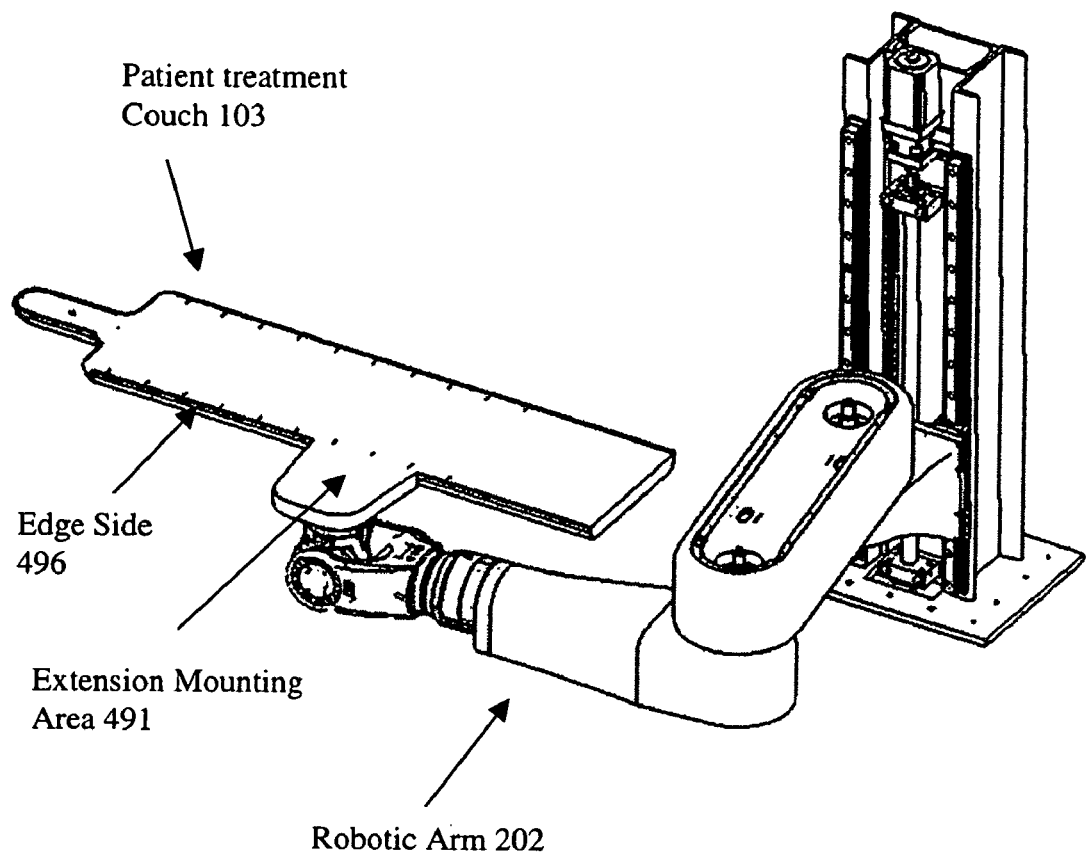
FIG. 4F illustrates an alternative embodiment of a robot arm mounting to a couch.

FIG. 4F illustrates an alternative embodiment of a robot arm mounting to a couch. In this embodiment, robotic arm 202 is mounted to patient treatment couch 103 on an extension mounting area 491 of the couch. It should be noted that the extension mounting area 491 may also be disposed at another location along the periphery of the patient treatment other than as shown in FIG. 4F. Alternatively, if the patient treatment couch 103 is sufficient thickness 213 (illustrated in FIG. 2B) in the mounting region, the robot arm 202 may be mounted directly to an edge side 496 of the couch without the use of extension mounting area 491. The mounting of robotic arm 202 on extension mounting area 491 (or, alternatively, on to edge side 496) may allow for the robotic arm to be out of the imaging field of view for all supported treatment positions (a 90 degree orientation position example is described below in relation to FIG. 4G). As previously discussed, in one embodiment, the patient treatment couch 103 is constructed from radiolucent material. However, the robotic arm 202 may not be constructed from such radiolucent material. Accordingly, the robotic arm 202 may not be imaged through and cause an imaging obstruction when it moves the patient treatment couch 103 in certain positions with respect to the imaging system.

Figure 4G:
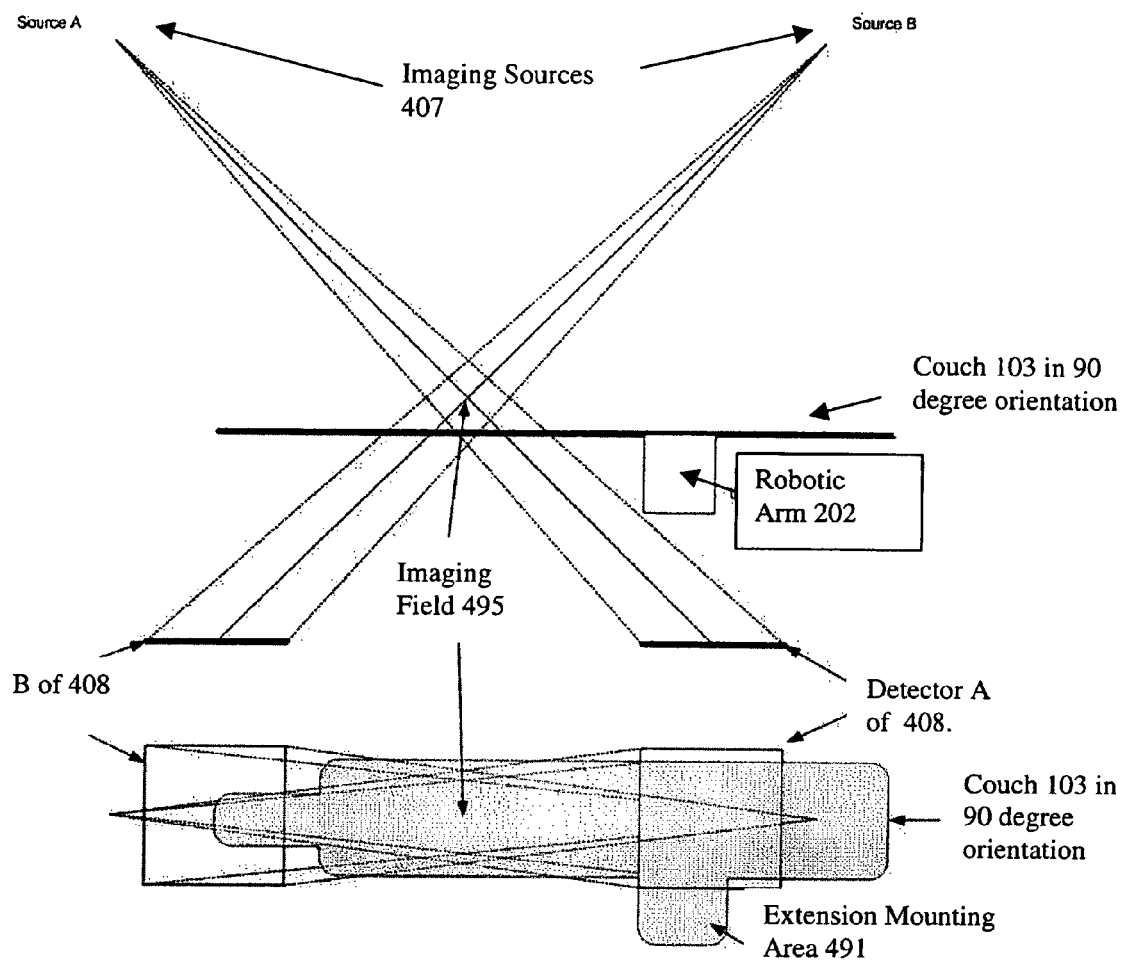
FIG. 4G illustrates a side and top view of one embodiment of the robotic arm mounting of to the couch of FIG. 4F in relation to an imaging system.

FIG. 4G illustrates a side and top view of one embodiment of the robotic arm mounting of to the couch of FIG. 4F in relation to an imaging system. As discussed above in relation to FIGS. 4A and 4B, the imaging system used with the robotic patient positioning assembly 100 and the robot-based linac system 406 may include two x-ray imaging sources (Source A and Source B) 407 and two imaging detectors (Detector A and Detector B) 408. In the orientation of the patient treatment couch 103 with respect to the detectors 408 illustrated in FIGS. 4A and 4B, the robotic arm 202 may not interfere or obstruct the imaging field of view of the detectors. However, when the robotic arm 202 orients the patient treatment couch 103 at approximately 90 degrees with respect to the orientation of FIGS. 4A and 4B, the robot arm 202 may cause an imaging obstruction in certain positions when mounted as shown in FIGS. 4A and 4B. FIG. 4G illustrates the patient treatment couch oriented at a 90 degree position with respect to the configuration of the couch and detectors illustrated in FIGS. 4A and 4B. For example, in this 90 degree orientation (and at other orientations), by using an extension mounting area 491 (or edge side 496 mounting) for the robot arm 202, the robotic arm 202 may be maintained substantially outside the imaging field 495 of the imaging system (e.g., x-ray imaging sources 407 and imaging detectors 408).

Figure 5:
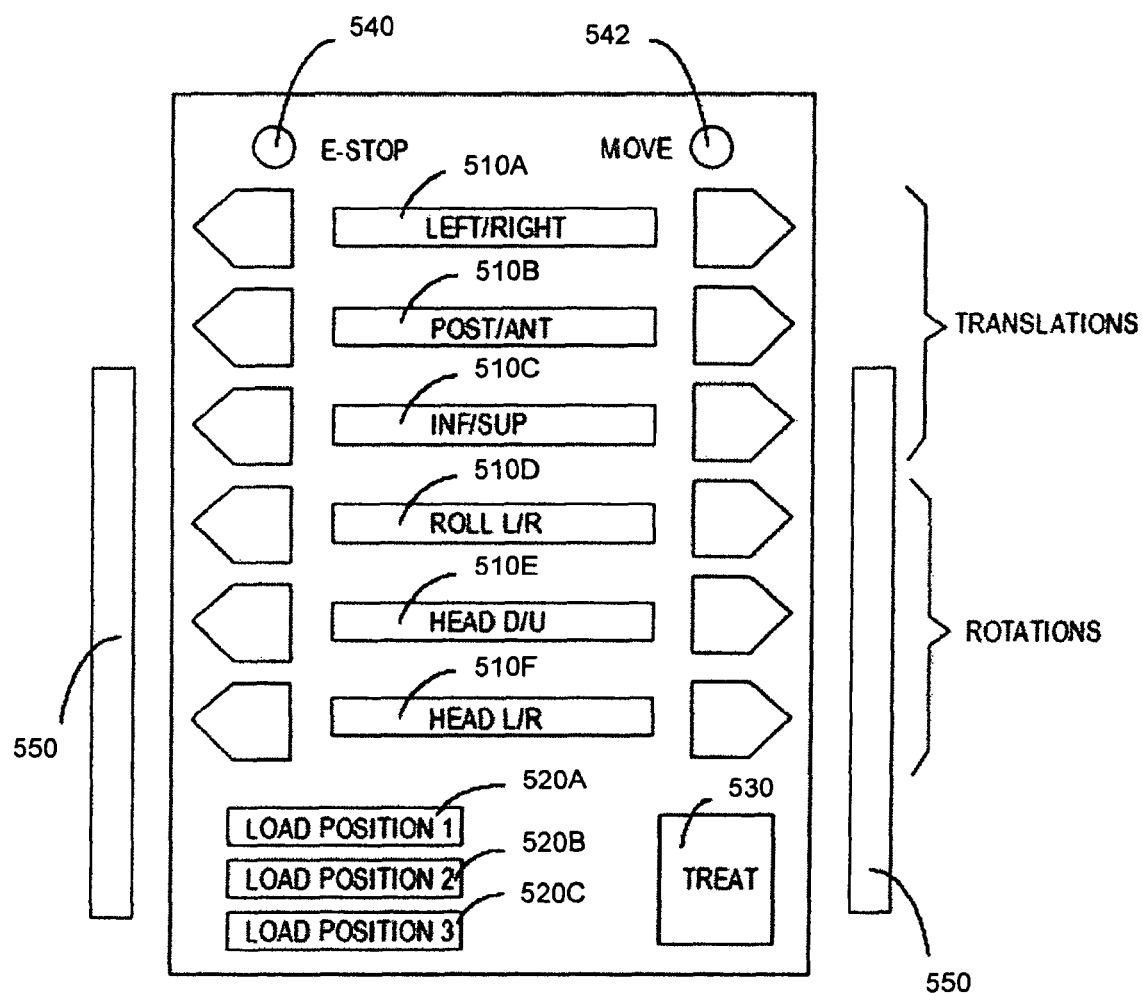
FIG. 5 illustrates one embodiment of a schematic diagram of a handheld user interface unit.

FIG. 5 illustrates one embodiment of a schematic diagram of a handheld user interface unit. The user interface unit 500 may affect computer control of the at least five rotational DOF and one substantially vertical, linear DOF of the robot-controlled patient treatment couch 103. In an exemplary embodiment, the user interface unit 500 includes: a bus interface for connecting the patient treatment couch 103 to the treatment system primary workstation including the controller 101, sensor system 104, imaging system 107, robotic arm 102, the therapeutic radiation treatment system 106; and at least one user interface unit 105, such as user interface unit 500 for allowing the user to interface with the controller 101 to interactively control the motion of the robotic patient positioning assembly 100; and a hardware interface to the treatment system E-stop (emergency stop) circuitry. The bus interface may be an Ethernet bus interface that can be connected to the treatment system primary workstation. The hardware interface to the E-stop circuitry may disable computer-controlled motions of the robotic patient positioning assembly 100 when any E-stop is engaged.

The E-stop mechanism may be operable to stop computer-controlled motion of the robotic patient positioning assembly 100. In one embodiment, the "System E-stop" may be an emergency lockout mechanism, capable of shutting down any and all radiation, and any and all motion. In other words, the "System E-stop" may shut down at least the following: 1) generation of therapeutic x-ray beams by the treatment x-ray source of the therapeutic radiation treatment system 106; 2) any motion of the treatment x-ray source and/or the robotic arm of the therapeutic radiation treatment system 106; 3) any motion of the robotic arm 102 and the patient treatment couch 103; and 4) the imaging system 107.

The user interface unit 500 may allow the user or operator to interactively participate in controlling the motion of the robotic arm 102 and the patient treatment couch 103, by implementing one or more user-selectable functions. In one embodiment, the user interface unit 500 may be a remote control unit. Alternatively, the user interface unit may be a graphical user interface unit, as described below. These user-selectable functions may include, but are not limited to, the following: 1) a function that allows the user to power on the patient treatment couch 103, so that the acquisition of the position of the patient treatment couch 103 can be initiated; 2) a function that allows the user to activate the x-ray imaging system 107, so that the acquisition of real time or near real time images of the target can be initiated; 3) a function for allowing the user to move the patient treatment couch 103 to one or more pre-programmed loading positions, which facilitates the loading of the patient onto the patient treatment couch 103 in a desired manner; 4) a function for allowing the user to move the patient treatment couch 103 to a pre-programmed "TREAT" position, which may be the default treatment position; 5) a function for displaying to the user the translations and rotations corresponding to the patient treatment couch 103 corrective motions needed to adjust the target position, in accordance with the information from the real time or near real time images; 6) a function for allowing the user to compare the translations and rotations with respective pre-specified limits for each translation and rotation; 7) a function for allowing the user to modify one or more of the pre-specified limits; and 8) a function for allowing the user to verify that the translations and rotations fall below the pre-specified limits, and thereupon activate the treatment x-ray source of the therapeutic radiation treatment system 106 to initiate treatment delivery.

In one exemplary embodiment, the user interface unit 500 may be a handheld remote control unit (e.g., handheld pendant) that provides a user with remote control capabilities for remote control of the motion of the robotic arm 102 and patient treatment couch 103. User interface unit 500 of FIG. 5 may be a handheld pendant, and may include a number of button icons respectively associated with these user-selectable functions. The handheld remote control unit 500 may provide controls to manually adjust the patient's position, and status indicators related to the motions of the robotic patient positioning assembly 100.

In the illustrated embodiment, the handheld remote control unit 500 includes motion switches: six sets of axes motion control switches 510A-510F, three loading position switches 520A, 520B, and 520C, and a treat switch 530. The axes motion control switches may provide bi-directional manual control of each degree of freedom via a pushbutton. The axes motion control switches may cause movement of the desired axes (three rotational axes: left/right (510A), posterior/anterior (510B), inferior (towards the feet)/superior (towards the head) (510C); three rotational axes: roll left/right (510D), head down/up (510E), head left/right (510F)) in the desired direction, as long as the switch is held down and motion is disabled. The loading switches 520A, 520B, and 520C may each initiate a programmed motion, if motion is enabled, that causes the patient treatment couch 103 to automatically move to the fully retracted, fully lowered loading position without any further operator action. The controller 101 may have one or more pre-programmed loading positions, and alternatively, a user may manually set a loading position for a patient through the handheld user interface unit 500 or a computer interface 600 illustrated in FIG. 6. The controller 101 may store the loading position for a particular patient for future treatment. The treat switch 530 may initiate a programmed motion, if motion is enabled, that causes the patient treatment couch 103 to move to a position defined by the controller 101 and previously downloaded to the patient treatment couch 103.

The remote control unit 500 may also include a pair of motion enable switches 550. Depressing one or both switches may enable all motion switches (axes motion control, loading positions, and treat), and overrides the System E-stop, if present, although it may not override any table E-stop switches. Releasing one or both of the enable switches while a programmed motion is occurring may cause that motion to stop.

The remote control unit 500 may also include a pair of status indicators 540 and 542, which may be light emitting diodes (LEDs) that provide an indication of whether motions are enabled and being accepted. In the illustrated embodiment, the E-stop LED 540 may be yellow when System E-stop is asserted, green when overridden by enable switches, and off when no System E-stop is asserted. The MOVE LED 542 may be green whenever a switch is pushed and motion is enabled, flashing green when a programmed movement is occurring, and yellow when the table E-stop is engaged.

The remote control unit 500 may also include a GoTo switch (not shown), allowing the user to access stored locations. The remote control unit 500 may also include display capabilities (not shown), for example to display to the user the translations and rotations, or to display informational messages to the user. The remote control unit 500 may also include absolute and relative position display/input modes (not shown). In another embodiment, the remote control unit 500 may also include a switch for activating the sensor system 104 to initiate detecting the position of the patient treatment couch 103.

Figure 6:
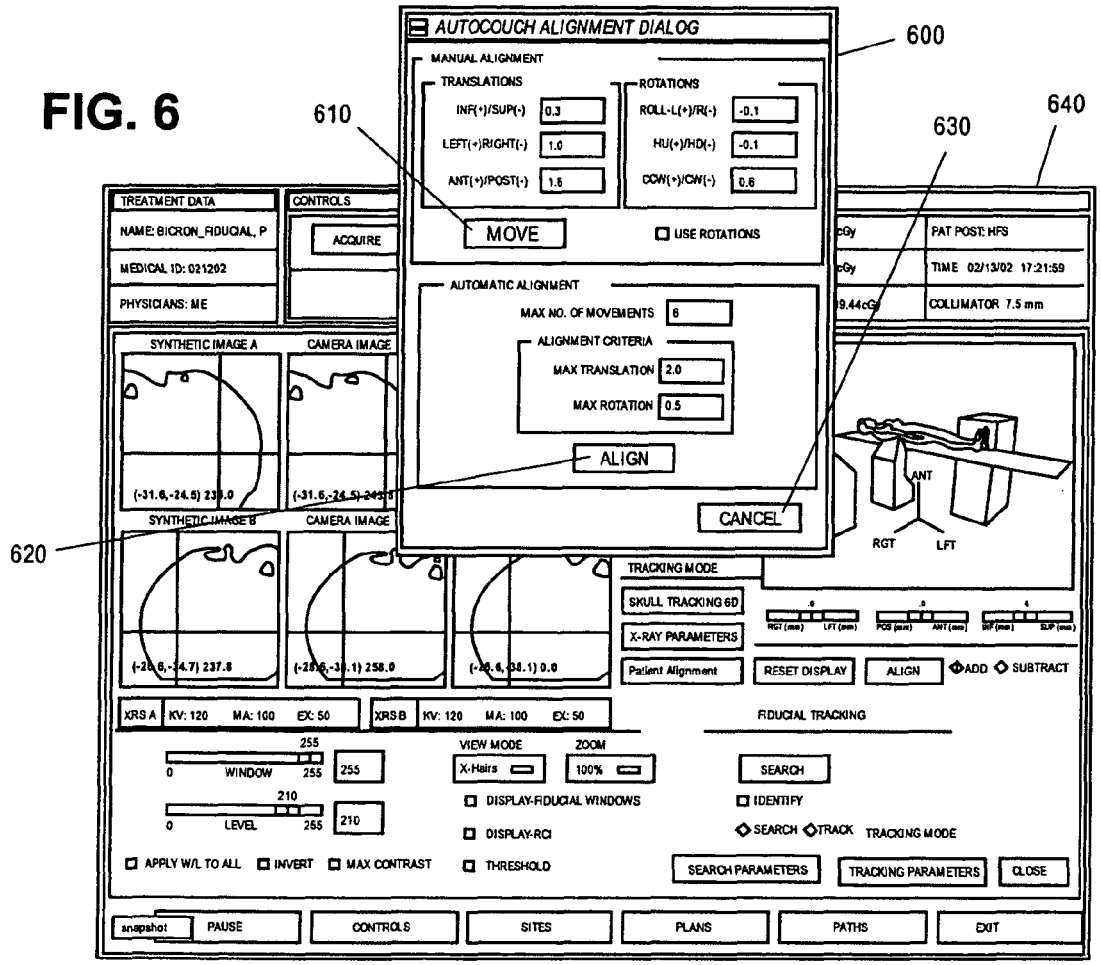
FIG. 6 illustrates an exemplary embodiment of a user interface screen, launched onto a treatment delivery display screen.

One or more user interface screens on the user control console of the primary workstation of the CyberKnife® radiosurgery system, may allow the user to inspect, initiate, and interactively control the motion of the robotic patient positioning assembly 100 for positioning the patient. FIG. 6 illustrates an exemplary embodiment of a user interface screen 600, launched into a treatment delivery screen 640 of the primary workstation. In the illustrated embodiment, the user interface screen 600 may provide to the user an integrated patient treatment couch position display, and patient treatment couch motion control capabilities. The user interface screen 600 provides sub-options to adjust translations only, or rotations only or all degrees of freedom available together.

In one embodiment, the user interface screen 600 includes button icons that allow the user to activate the sensor system 104 to detect the position of the patient treatment couch 103.

In the illustrated embodiment, an ALIGN COUCH button in the treatment delivery screen 640 may launch the user interface screen 600. The user interface screen 600 may include a number of fields, with different functions. These fields may include translation and rotation fields, which are initially filled with the corrective motions of the robotic patient positioning assembly 100 returned by the TLS unit of the controller 101. If no valid patient treatment couch corrective motions are available, these fields are left blank. The translation and rotation fields may be editable.

In the illustrated embodiment, the user interface screen 600 includes a MOVE button 610, an "AUTO ALIGN" button 320, and a "CANCEL" button 630. The "MOVE" button 610 moves the patient treatment couch 103 by the amount of translations and rotations indicated. If the "Apply rotation" field is unchecked, the patient treatment couch 103 may be moved only in rotational axes. The "AUTO ALIGN" button 620 initially moves the patient treatment couch 103 by the amount of translations and rotations indicated, and proceeds to acquire images through the imaging system 107 and correct patient treatment couch 103 positions automatically until pre-specified "Auto align limits" are satisfied. This may mean that the translations and rotations are below the pre-specified limits, or the number of images indicated is taken. The "Auto align limits" fields are filled in from a system configuration file, but can be edited. The "CANCEL" button 630 will return to the Patient Alignment interface.

In one embodiment, the user interface screen 600 includes button icons that allow the user to adjust imaging parameters, such as the intensity, energy, and duration of the x-rays in the imaging beams generated by the imaging system 107; the number of real time or near real time images to be acquired; the selection and de-selection of fiducials; and rigid body parameters.

Figure 7:
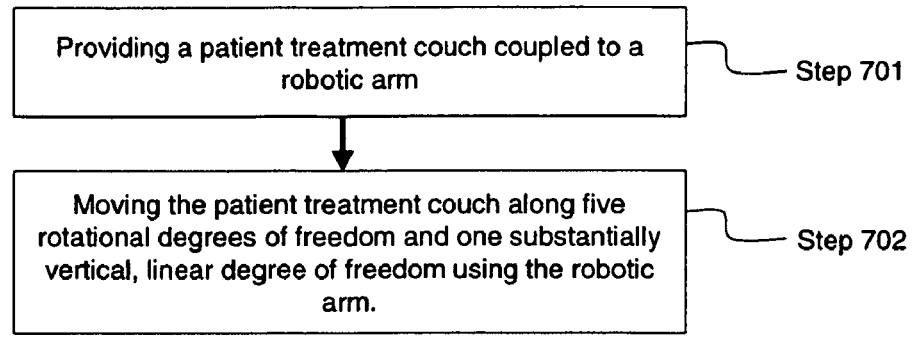
FIG. 7 illustrates a one embodiment of a method for positioning a patient treatment couch using a robotic arm.

FIG. 7 illustrates a one embodiment of a method for positioning a patient treatment couch using a robotic arm. The method may include providing a patient treatment couch 103 coupled to a robotic arm 102, step 701, and moving the patient treatment couch 103 along five rotational degrees of freedom and one substantially vertical, linear degree of freedom using a robotic arm 102, step 702. In one embodiment, the five rotational degrees of freedom include two horizontal rotational axes (Axes 3, and 2 of FIG. 2A) (e.g., x-, y-axes) and three rotational axes including a yaw axis, a pitch axis, and a roll axis (Axes 6, 5, and 4 of FIG. 2A), and the one substantially vertical, linear degree of freedom includes a substantial linear axis for translational movement of the patient treatment couch along a substantially vertical line in a coordinate axis (e.g., z-axis) substantially perpendicular to the two horizontal coordinate axes (e.g., x-, and y-axes).

In another embodiment, the method for positioning a patient treatment couch 103 using a robotic arm 102 may include providing a patient treatment couch 103 coupled to a robotic arm 102, and moving the patient treatment couch 103 along six rotational degrees of freedom and one substantially vertical, linear degree of freedom using a robotic arm 102. In one embodiment, the six rotational degrees of freedom include three rotational axes (Axes 3, 2, and 1 of FIG. 3A) (e.g., x-, y-, & z-) and three rotational axes including a yaw axis, a pitch axis, and a roll axis (Axes 6, 5, and 4 of FIG. 3A), and the one substantially vertical, linear degree of freedom includes a substantial linear axis for translational movement of the patient treatment couch along a substantially vertical line in a coordinate axis (e.g., z-axis) substantially perpendicular to the two horizontal coordinate axes (e.g., x-, and y-axes).

In one embodiment, the method may include sustaining a load on the patient treatment couch up to five hundred pounds (500 lbs) within a deflection error 261 of approximately zero to five millimeters (0 to 5 mm). Alternatively, the patient load on the patient treatment couch may be up to two thousand pounds (2000 lbs) in a static position.

The method may further include moving the patient treatment couch along a single one of the rotational axes and the rotational axes without moving the patient treatment couch along a different one said axis throughout an entire range of motion of the patient treatment couch. The method may also include providing a controller for moving the robotic arm and patient treatment couch along five or six rotational degrees of freedom and one substantially vertical, linear degree of freedom. The method may also include providing a user interface unit coupled to the controller for manually moving the robotic arm and patient treatment couch along at least one of five and six rotational degrees of freedom and one substantially vertical, linear degree of freedom.

In one embodiment, moving the patient treatment couch along five rotational degrees of freedom and one substantially vertical, linear degree of freedom using the robotic arm includes rotating the patient treatment couch along the yaw-axis using a tool-yaw joint of the robotic arm, rotating the patient treatment couch along the pitch-axis using a tool-pitch joint of the robotic arm, rotating the patient treatment couch along the roll-axis using a tool-roll joint of the robotic arm, rotating the patient treatment couch along the two horizontal rotational axes using a elbow joint and a shoulder joint, and translating the patient treatment couch along a substantially vertical, linear axis using a track and track mount assembly perpendicular to the two horizontal rotational axes. In another embodiment, moving the patient treatment couch further includes rotating the patient treatment couch along an additional translational axis using an additional shoulder joint, totaling six rotational degrees of freedom and one substantially vertical, linear DOF. The six DOF may include three rotational axes for translational movements along mutually orthogonal x-, y-, and z-coordinate axes; and three rotational axes for roll-, pitch-, and yaw-rotational movements about x-, y-, and z-axes, respectively. The one substantially vertical, linear DOF may include a substantial linear axis for translation along a substantially vertical line in a z-coordinate axis perpendicular to the horizontal, x-, and y-coordinate axes.

Figure 8:
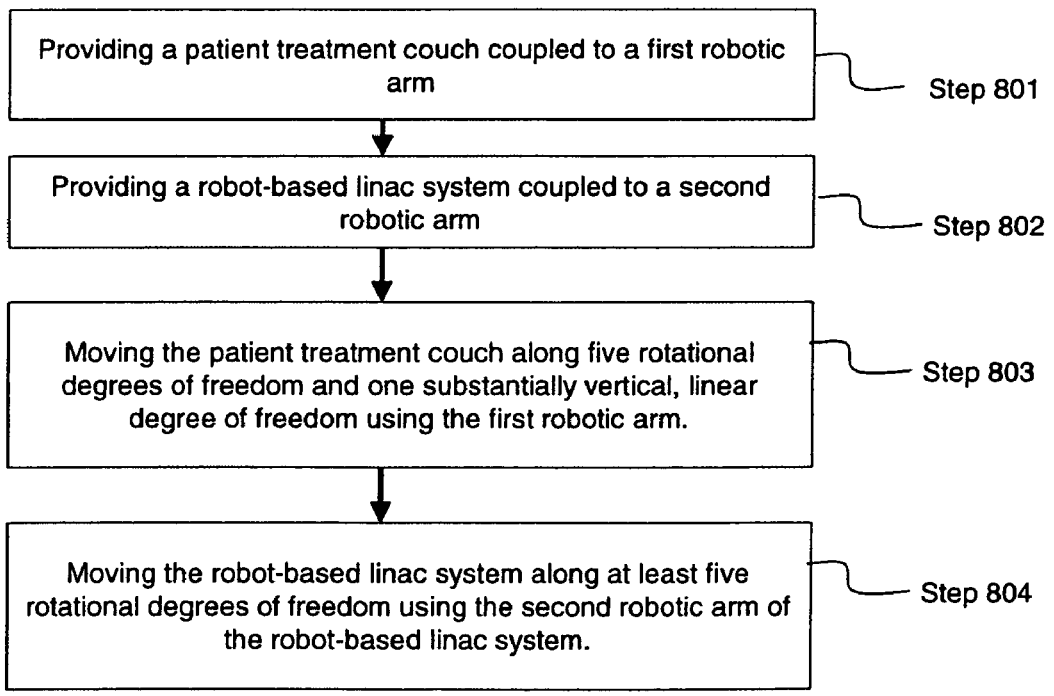
FIG. 8 illustrates another embodiment of a method for positioning a patient treatment couch using a robotic arm and a robot-based linear accelerator system.

FIG. 8 illustrates another embodiment of a method for positioning a patient treatment couch using a robotic arm and a robot-based linac system 406. The method may include providing a patient treatment couch coupled to a first robotic arm, step 801; providing a robot-based therapeutic radiation treatment system using a second robotic arm, step 802; moving the patient treatment couch along five rotational degrees of freedom and one substantially vertical, linear degree of freedom using the first robotic arm, step 803; and moving the robot-based linac system along at least five degrees of freedom using the second robotic arm of the robot-based therapeutic radiation treatment system, step 804. In another embodiment, the method may further include providing a controller coupled to the robot-based therapeutic radiation treatment system and the robotic arm.

In one embodiment, moving the patient treatment couch and the robot-based linac system may include dynamically coordinating an orientation and position of the patient treatment couch and a therapeutic radiation source of the robot-based linac system using the controller. Dynamically coordinating the orientation and position of the patient treatment couch and the therapeutic radiation source may increase a number of treatment targets within a mechanical range of motion of the robotic arm. In another embodiment, moving the patient treatment couch and the robot-based linac system includes aligning a therapeutic radiation source of the robot-based linac system with a treatment target within a patient disposed on the patient treatment couch. In another embodiment, moving the patient treatment couch and the robot-based linac system further includes positioning the patient treatment couch and the therapeutic radiation source to create a treatment target in a previously obstructed location within a mechanical range of motion of the robotic arm and the robot-based linac system.

In one embodiment, the previously obstructed location may be caused by an obstruction of a possible collision, for example, between either the patient treatment couch 103, therapeutic radiation source 409, or their corresponding robotic arms with the robotic arm 202, the patient treatment couch 103, the therapeutic radiation source 409, x-ray imaging sources 407, detectors 408, and/or other components of the robot-based linac system 406. Alternatively, the previously obstructed location may be caused by an obstruction of the radiation beam of the therapeutic radiation source 409 with the robotic arm 202, the patient treatment couch 103, the therapeutic radiation source 409, x-ray imaging sources 407, detectors 408, and/or other components of the robot-based linac system 406.

In operation, an approximate treatment location for the patient may be computed, as part of the treatment planning process. When the treatment plan is loaded into the controller 101, the approximate treatment location may be downloaded into the patient treatment couch 103. The operator positions the patient on the patient treatment couch 103, and applies any restraining devices. The operator then presses the "TREAT" button in the handheld user interface unit 500 (shown in FIG. 5), and the patient treatment couch 103 automatically moves to bring all of its degrees of freedom to the stored positions. Alternatively, the "Treat" command could also be issued from the user interface screen 600. The number of axes to move simultaneously may be limited by design to ensure that power demands are not excessive and that the patient is comfortable with the number of simultaneous motions taking place.

The operator then exits the treatment room and using the user interface screen 600 (shown in FIG. 6) on the workstation or dedicated control panel, may command the system to align the patient to within desired tolerances. The user interface screen 600 may allow the user to enter parameters such as the maximum number of real time or near real time images to take during the alignment process, and the desired tolerances for position and orientation. The user interface screen 600 also may allow the errors associated with each image to be displayed.

After obtaining a satisfactory alignment, the therapeutic radiation treatment system 106 may be commanded to begin treatment. As part of the treatment, real time or near real time images may be obtained periodically by the imaging system 107, to check whether the patient moves during the treatment. If the patient does move, the treatment delivery can be paused automatically or manually by the operator, and the patient can be realigned, by effecting appropriate corrective motions of the robotic patient positioning assembly 100. At the conclusion of the treatment, the operator reenters the treatment room and uses the "Load Position" buttons on the handheld user interface unit 500 to return the patient treatment couch 103 to the loading/unloading position for patient unloading. Alternatively, the system may issue the command to return to the original loading position from the user interface screen 600.

In one embodiment, components of the robotic arm 202 or robotic arm 302 may include touch-sensing material on the components' exterior. In another embodiment, the exterior of the components may be coated with contact foam. Alternatively, other materials may be used to prevent components of the robotic arm 202 or of robotic arm 302 from crushing or knocking over the operator. Specific details regarding the touch-sensing material and contact foam that are known to those of ordinary skill in the art have not been included as to not obscure the discussion regarding coating the exterior of the robotic arms 202 and 302 with material to prevent the operator from being knocked over or crushed by the robotic arm.

Following is a more detailed description of another embodiment of operation of the robotic patient positioning assembly described above.

The first stage is the initial patient set-up stage. During this stage, the treatment planning files are downloaded, prior to patient entry into the treatment room. During the download of treatment files, the treatment position of the patient treatment couch 103 may be downloaded into the controller 101. The treatment position of the patient treatment couch 103 may be one of: a) a default patient treatment couch position for the beam path set selected; and b) a treatment position for the patient, the last time the same plan was used. Before the patient walks into the treatment room, one of the loading position buttons on the handheld remote control unit 500 may be pressed, so as to position the patient treatment couch 103 in a pre-defined comfortable position for the patient to get onto the patient treatment couch 103. The patient may be then immobilized, for example using a thermoplastic mask and or other immobilization devices.

The "TREAT" button on the handheld remote control unit 500 may be used to position the patient treatment couch 103 to the nominal treatment position. For head or body treatments, or if this is a second or subsequent treatments for the patient with the same plan, the nominal treatment position may be adequate for further automatic positioning, and the operator can proceed to the user control console for automatic positioning of the patient. Otherwise, the patient treatment couch 103 may be further manually adjusted, using the handheld remote control unit 500, so that the anatomical target region of interest may be within the imaging field of view. The operator then proceeds to the user interface screen 600, for automatic positioning of the patient.

The next stage may be the initial image acquisition stage. During this stage, the operator may acquire images, using the ACQUIRE button on the patient alignment screen in the user interface screen 600 (shown in FIG. 6). If necessary, imaging parameters may need to be adjusted. Some examples of these parameters are: x-ray parameters; de-selection of fiducials that may have migrated or otherwise difficult to track; and adjustment of rigid body parameters.

The next stage may be the one-time patient treatment couch alignment stage. The user selects the "AUTO COUCH" button on the patient alignment screen. This brings up a Couch Adjustment interface screen of user interface screen 600, which contains the initial corrections obtained from the TLS unit of the controller 101. The initial corrections from TLS may be editable. The "MOVE" button moves the patient treatment couch 103 by the amount of corrections indicated in the window. The option to disable rotation corrections may also be available. The "AUTO ALIGN" button may perform the first correction, and proceeds to complete the automatic alignment.

The next stage may be the automatic patient treatment couch alignment stage. The "AUTO ALIGN" button in the Couch Adjustment interface screen may perform the automatic alignment. Auto Align may start by making the initial correction in the Couch Adjustment interface, and proceeds to take additional images and perform the correction from the image, until one of the following conditions are met: the desired number of images in the Auto Alignment phase are acquired, and/or the residual corrections fall below the limits specified in the Auto Alignment interface.

The next stage may be the patient re-alignment stage. Patient re-alignment may be entered whenever the system encounters a recoverable error (including operator pause), and the system is resumed from this state. Patient re-alignment may be handled the same way as patient alignment. In other words, after the initial acquisition, further adjustments can be done automatically using the "AUTO ALIGN" button in the Couch Adjustment interface.

The final stage may be the treatment delivery stage. Treatment delivery may be initiated when the corrective motions for the patient treatment couch 103 fall below pre-specified limits for translations and rotations of the robotic arm 102 and patient treatment couch 103. The corrective motions downloaded to the controller 101 of the robotic patient positioning assembly 100 may include translations and the specified set of rotations. The robot may move to the nominal position for the node, correct by the specified translation and rotation, and then enable the x-ray beam generator of the therapeutic radiation treatment system 106. At the end of dose delivery for the node, the robot of the therapeutic radiation treatment system 106 may proceed to the next node in this nominal position.

The controller 101 may include software for error detection, reporting, and correction. In one embodiment, the error handling software includes "operator pause" functionality. This functionality allows the user to stop image acquisition, if one is in progress, and return to a target alignment or realignment mode. The user may also stop the motion of the robotic patient positioning assembly 100, if one is in progress, and return to the target alignment/realignment mode. The user may also stop subsequent image acquisitions and motions of the robotic patient positioning assembly 100, if the "auto alignment" mode is in progress.

In one embodiment, the error handling software also includes a functionality for handling TLS (target locating system) errors. Appropriate TLS errors, such as soft algorithm errors, and/or E-stop for hardware errors, are reported. Upon acknowledgement of the error, the controller 101 may return to the alignment or re-alignment state. The user may stop subsequent image acquisitions and motions of the robotic patient positioning assembly 100, if "auto alignment" is in progress. During the initial alignment, the "patient out of bounds" error may be disabled, but the "TREAT" button may be disabled until the patient is within bounds.

In one embodiment, the error handling software includes functionality for handling table interface errors. Table interface errors such as communication errors are handled as soft errors, which require user acknowledgment, but do not engage an E-stop. In one embodiment, the error handling software may include functionality for handling E-stops. In this embodiment, an E-stop stops computer-controlled motion of the robotic patient positioning assembly 100, using a dual redundant mechanism. The controller software stops generating any further motion command signals. The patient treatment couch controller hardware may be disabled from patient treatment couch movement when an E-stop is engaged. Even when the E-stop is engaged, the patient treatment couch may be capable of moving using the handheld user interface unit 500. On resumption from pause or a recoverable E-stop, the E-stop may be cleared by system reset from the operator console, which then goes into a patient re-alignment state. At this stage, the user can use auto-align to refine the patient position. The "RESUME" button on the patient re-alignment screen enables resumption of treatment delivery.

In one embodiment of positioning a patient location and orientation during medical operations includes positioning a patient treatment couch 103 along two horizontal rotational axes (x-, y-) (Axes 2 and 3 of FIG. 2A) and three rotational axes (yaw, pitch, and roll) (Axes 6, 5, and 4 of FIG. 2A); and positioning the patient treatment couch 103 along one substantially vertical, linear axis (z-) (Axes 1 of FIG. 2A).

In another embodiment of positioning a patient location and orientation during medical operations includes positioning a patient treatment couch 103 along three rotational axes (x-, y-, z-) (Axes 3, 2, and 1 of FIG. 3A), and three rotational axes (yaw, pitch, and roll) (Axes 6, 5, and 4 of FIG. 3A); and positioning the patient treatment couch 103 along one substantially vertical, linear axis (z-) (Axes 7 of FIG. 3A).

In one embodiment, the patient treatment couch 103 may be provided with an at least two directions loading mechanism, which, in operation, can load or unload the patient in horizontal manners and vertical manners. The robotic patient positioning assembly 100 includes the patient treatment couch 103, which, in a vertical loading manner, may be positioned oblique to the horizontal plane, for example at approximately seventy degrees (70°) with respect to the horizontal plane. After the patient is secured on the patient treatment couch 103, the patient treatment couch 103 may position the patient to the treatment position within the workspace. In one embodiment, the top surface of the patient treatment couch 103 may be provided with a patient specific mold, which may be customized to fit the body curve of the patient. In another embodiment, one end of the patient treatment couch 103 may be provided with a footplate for supporting the patient's feet in vertical loading manners. In another embodiment, the patient treatment couch 103 may be provided with a chair-like supporting device, and the patient treatment couch 103 may be adapted to provide a sitting position for loading and/or unloading, and/or for treating the patient.

Alternatively, the patient treatment couch 103 may also provide loading/unloading positions as shown in FIG. 4A, sitting loading/unloading positions, and other loading/unloading positions that are set for the convenience of particular patients.

It should be noted that more rotatable and/or slidable sections, for example, an additional arm, may be added to the robotic patient positioning assembly 100 to obtain more flexibility and a greater reach of the patient treatment couch 103. Alternatively, the robotic patient positioning assembly 100 can include fewer sections than the robotic patient positioning assembly 100, for example, including only an elbow assembly instead of both the elbow assembly and shoulder assembly. The translational and rotational movements of the robotic patient positioning assembly 100 may be controlled manually and/or automatically by the computer controller 101.

In the foregoing specification, embodiments of the invention have been described with reference to specific exemplary embodiments thereof. It will, however, be evident that various modifications and changes may be made thereto without departing from the broader spirit and scope of the present embodiments as set forth in the claims. The specification and drawings are, accordingly, to be regarded in an illustrative rather than a restrictive sense.

What is claimed:

1. An apparatus, comprising:
   a patient treatment couch;
   a robotic arm coupled to the patient treatment couch, the robotic arm configured to move using five rotational degrees of freedom and one substantially vertical, linear degree of freedom;
   a controller coupled to the robotic arm;
   an imaging system coupled to the controller to generate a plurality of images of a patient; and
   a therapeutic radiation treatment system comprising a therapeutic radiation source, the therapeutic radiation treatment system configured to position the therapeutic radiation source at a plurality of locations of a workspace.

2. The apparatus of claim 1,
   wherein the therapeutic radiation treatment system is coupled to the controller, wherein the controller is configured to control movement of at least one of the robotic arm and the therapeutic radiation treatment system to align the therapeutic radiation source with a treatment target within a patient disposed on the patient treatment couch.

3. The apparatus of claim 2, wherein the therapeutic radiation treatment system is robot-based linear accelerator system.

4. The apparatus of claim 3, wherein orientation and position of the therapeutic radiation source of the robot-based linear accelerator system and the patient treatment couch are dynamically coordinated by the controller.

5. The apparatus of claim 4, wherein the controller is configured to position the patient treatment couch and the therapeutic radiation source of the robot-based linear accelerator system to deliver radiation to the treatment target at a location that was previously obstructed, wherein the previously obstructed location was caused by a positioning restriction within a mechanical range of motion of the robotic arm and the robot-based linear accelerator system.

6. The apparatus of claim 5, wherein the positioning restriction comprises at least one of obstructions of a possible collision with at least one of the robotic arm coupled to the patient treatment couch and the therapeutic radiation source with at least one of the treatment couch, the therapeutic radiation source, and the imaging system.

7. The apparatus of claim 5, wherein the positioning restriction comprises obstructions of a radiation beam of the therapeutic radiation source with at least one of the treatment couch, the therapeutic radiation source, and the imaging system.

8. The apparatus of claim 1, wherein the imaging system has an imaging field of view and wherein the robotic arm is coupled to the patient treatment couch at an extension mounting area to maintain the robotic arm outside the field of view of the imaging system when the robotic arm moves the patient treatment couch.

9. A method comprising:
   providing a patient treatment couch coupled to a first robotic arm;
   providing a robot-based linear accelerator system coupled to a second robotic arm;

moving the patient treatment couch using five rotational degrees of freedom and one substantially vertical, linear degree of freedom of the first robotic arm; and moving the robot-based linear accelerator system among different locations of a workspace.

10. The method of claim 9, further comprising moving the robot-based linear accelerator system using at least two degrees of freedom of the second robotic arm of the robot-based linear accelerator system.

11. The method of claim 9, wherein moving the robot-based linear accelerator system comprises using at least five degrees of freedom of the second robotic arm of the robot-based linear accelerator system.

12. The method of claim 9, further comprising providing a controller coupled to the robot-based linear accelerator system and the second robotic arm.

13. The method of claim 12, wherein moving the patient treatment couch and the robot-based linear accelerator system further comprise dynamically coordinating orientation and position of the patient treatment couch and a therapeutic radiation source of the robot-based linear accelerator system using the controller.

14. The method of claim 13, wherein dynamically coordinating the orientation and position of the patient treatment couch and the therapeutic radiation source increases a total usable surface area of the therapeutic radiation source within a mechanical range of motion of the second robotic arm.

15. The method of claim 9, wherein moving the patient treatment couch and the robot-based linear accelerator system further comprises aligning a therapeutic radiation source of the robot-based linear accelerator system with a treatment target within a patient disposed on the patient treatment couch.

16. The method of claim 12, wherein moving the patient treatment couch and the robot-based linear accelerator system further comprises positioning the patient treatment couch and the therapeutic radiation source to deliver radiation to the treatment target at a location that was previously obstructed, wherein the previously obstructed location was caused by a positioning restriction within a mechanical range of motion of the robotic arm and the robot-based linear accelerator system.

17. The method of claim 16, wherein dynamically coordinating the orientation and position of the patient treatment couch and the therapeutic radiation source further comprises avoiding the positioning restriction.

18. The method of claim 17, wherein the positioning restriction comprise obstructions of the therapeutic radiation source due to at least one of an x-ray imaging source and an x-ray imaging detector.

19. The method of claim 9, further comprising:
providing an imaging system having an imaging field of view; and
maintaining the patient treatment couch substantially outside of the imaging field of view for all supported treatment positions.

20. The apparatus of claim 1, wherein the five degrees of freedom comprise:
two rotational axes for translational movements of the patient treatment couch in mutually orthogonal horizontal coordinate x- and y-axes; and
three rotational axes for roll-, pitch-, and yaw-rotational movements of the patient treatment couch about the x-axis, the y-axis, and a z-axis, respectively, and wherein the one substantially vertical, linear degree of freedom comprises a substantial linear axis for translational movements of the patient treatment couch along a substantially vertical line in the z-axis substantially perpendicular to the horizontal coordinate x- and y-axes.

21. The apparatus of claim 1, wherein the controller is configured to move the patient treatment couch along the substantially vertical, linear axis throughout substantially an entire range of motion of the patient treatment couch without using the five rotational degrees of freedom.

22. The apparatus of claim 1, wherein the robotic arm is vertically mounted to at least one of a vertical side of a column or a wall.

23. The apparatus of claim 22, wherein the column is mounted to at least one of a floor and a ceiling.

* * * * *